US007838729B2

(12) United States Patent
Feng et al.

(10) Patent No.: US 7,838,729 B2
(45) Date of Patent: Nov. 23, 2010

(54) CHLOROPLAST TRANSIT PEPTIDES FOR EFFICIENT TARGETING OF DMO AND USES THEREOF

(75) Inventors: Paul C. C. Feng, Wildwood, MO (US); Marianne Malven, Ellisville, MO (US); Stanislaw Flasinski, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 413 days.

(21) Appl. No.: 11/758,659

(22) Filed: Jun. 5, 2007

(65) Prior Publication Data

US 2009/0029861 A1 Jan. 29, 2009

Related U.S. Application Data

(60) Provisional application No. 60/891,675, filed on Feb. 26, 2007.

(51) Int. Cl.
*A01H 1/00* (2006.01)
*A01H 5/00* (2006.01)
*C12N 15/82* (2006.01)

(52) U.S. Cl. .................. 800/278; 800/298; 800/300; 800/300.1; 800/312; 800/314; 536/23.4; 536/23.6; 536/23.7; 435/410; 435/413; 435/415; 435/418; 435/419

(58) Field of Classification Search ............... None
See application file for complete search history.

(56) References Cited

U.S. PATENT DOCUMENTS

| | | | | |
|---|---|---|---|---|
| 4,816,403 | A | 3/1989 | Roy | 435/253.3 |
| 5,094,945 | A | 3/1992 | Comai | 436/6 |
| 5,254,799 | A | 10/1993 | De Greve et al. | 800/205 |
| 5,362,865 | A | 11/1994 | Austin | 536/24.1 |
| 5,445,962 | A | 8/1995 | Atallah et al. | 435/252.1 |
| 5,463,175 | A | 10/1995 | Barry et al. | 800/300 |
| 5,627,061 | A | 5/1997 | Jepson et al. | 800/288 |
| 5,633,435 | A | 5/1997 | Barry et al. | 800/288 |
| 5,633,437 | A | 5/1997 | Bernasconi et al. | 800/278 |
| 5,656,422 | A | 8/1997 | Crawford et al. | 435/4 |
| 5,670,454 | A | 9/1997 | Grossmann et al. | 504/244 |
| 5,728,925 | A | 3/1998 | Herrera-Estrella et al. | 800/300 |
| 5,939,602 | A | 8/1999 | Volrath et al. | 800/300 |
| 6,040,497 | A | 3/2000 | Spencer et al. | 800/288 |
| 6,268,549 | B1 | 7/2001 | Sailland et al. | 800/295 |
| 6,376,754 | B1 | 4/2002 | Schillinger et al. | 800/312 |
| 6,414,222 | B1 | 7/2002 | Gengenbach et al. | 800/300.1 |
| 6,586,367 | B2 | 7/2003 | Lee et al. | 504/127 |
| 6,613,963 | B1 | 9/2003 | Gingera et al. | 800/306 |
| 7,022,896 | B1 * | 4/2006 | Weeks et al. | 800/300 |
| RE39,247 | E | 8/2006 | Barry et al. | 800/300 |
| 7,105,724 | B2 | 9/2006 | Weeks et al. | 800/300 |
| 7,230,163 | B2 | 6/2007 | Becton et al. | 504/323 |
| 7,385,106 | B2 * | 6/2008 | Stein et al. | 800/298 |
| 7,405,074 | B2 | 7/2008 | Castle et al. | 536/23.2 |
| 7,405,347 | B2 | 7/2008 | Hammer et al. | 800/300 |
| 7,407,913 | B2 | 8/2008 | Lee et al. | 504/128 |
| 7,429,691 | B2 | 9/2008 | Zhang et al. | 800/278 |
| 7,462,481 | B2 | 12/2008 | Castle et al. | 435/320.1 |
| 7,622,641 | B2 | 11/2009 | McCutchen et al. | 800/300 |
| 2003/0041357 | A1 | 2/2003 | Jepson et al. | 800/300 |
| 2003/0083480 | A1 | 5/2003 | Castle et al. | 536/23.1 |
| 2003/0115626 | A1 | 6/2003 | Weeks et al. | 800/278 |
| 2003/0135879 | A1 | 7/2003 | Weeks et al. | 800/278 |
| 2004/0082770 | A1 | 4/2004 | Castle et al. | 435/320.1 |
| 2004/0097373 | A1 | 5/2004 | Lee et al. | 504/128 |
| 2004/0177399 | A1 | 9/2004 | Hammer et al. | 800/300 |
| 2005/0235379 | A1 | 10/2005 | Luo et al. | 800/290 |
| 2006/0235215 | A1 | 10/2006 | Cooper | 800/289 |
| 2007/0079393 | A1 | 4/2007 | McCutchen et al. | 800/278 |
| 2008/0015110 | A1 | 1/2008 | Clemente et al. | 800/300 |
| 2008/0119361 | A1 | 5/2008 | Feng et al. | 504/105 |
| 2008/0120739 | A1 | 5/2008 | Wan et al. | 800/300 |
| 2008/0305952 | A1 | 12/2008 | Arnevik et al. | 800/300 |
| 2009/0029861 | A1 | 1/2009 | Feng et al. | 800/300 |
| 2009/0081760 | A1 | 3/2009 | D'Ordine et al. | 435/189 |
| 2009/0105077 | A1 | 4/2009 | Bhatti et al. | 504/206 |

FOREIGN PATENT DOCUMENTS

| | | |
|---|---|---|
| CA | 2165036 | 6/1996 |
| WO | WO 97/41228 | 11/1997 |
| WO | WO 98/45424 | 10/1998 |
| WO | WO 00/29596 | 5/2000 |
| WO | WO 02/068607 | 9/2002 |
| WO | WO 03/034813 | 5/2003 |
| WO | WO 2004/009761 | 1/2004 |

(Continued)

OTHER PUBLICATIONS

Khalil et al., "Plasmid-mediated catabolism of dicamba by pseudomonsas species strain PXM," *Microbios*, 102:183-191, 2000.
Spencer et al., "Segregation of transgenes in maize," *Plant Molecular Biology*, 18:201-210, 1992.
Weeks et al., "Characterization of a bacterial system capable of degrading dicamba and evaluation of its potential in the development of herbicide-tolerant crops," *J. of Cellular Biochemistry*, Supplement 18A:91, 1994.
U.S. Appl. No. 60/884,854, filed Jan. 12, 2007, D'Ordine et al.
Becker et al., "The cab-m7 gene: a light-inducible, mesophyll-specific gene of maize," *Plant Mol. Biol.*, 20:49-60, 1992.

(Continued)

*Primary Examiner*—Eileen B O Hara
(74) *Attorney, Agent, or Firm*—Pamela J. Sisson, Esq.; SNR Denton US LLP

(57) ABSTRACT

The invention provides for identification and use of certain chloroplast transit peptides for efficient processing and localization of dicamba monooxygenase (DMO) enzyme in transgenic plants. Methods for producing dicamba tolerant plants, methods for controlling weed growth, and methods for producing food, feed, and other products are also provided, as well as seed that confers tolerance to dicamba when it is applied pre- or post-emergence.

33 Claims, 1 Drawing Sheet

FOREIGN PATENT DOCUMENTS

| WO | WO 2004/074443 | 9/2004 |
|---|---|---|
| WO | WO 2004/101797 | 11/2004 |
| WO | WO 2005/003362 | 1/2005 |
| WO | WO 2005/107437 | 11/2005 |
| WO | WO 2007/143690 | 12/2007 |
| WO | WO 2007/146706 | 12/2007 |
| WO | WO 2008/048964 | 4/2008 |
| WO | WO 2008/051633 | 5/2008 |
| WO | WO 2008/105890 | 9/2008 |

OTHER PUBLICATIONS

Bohlmann et al., "Purification and cDNA cloning of anthranilate synthase from *Ruta graveolens*: modes of expression and properties of native and recombinant enzymes," *Plant J.*, 7(3):491-501, 1995.
Clark et al., "Nucleotide sequence of a wheat (*Triticum aestivum* L.) cDNA clone encoding the waxy protein," *Plant Mol. Biol.*, 16(6):1099-1101, 1991.
Coruzzi et al., "Tissue-specific and light-regulated expression of a pea nuclear gene encoding the small subunit of ribulose-1,5-bisphosphate carboxylase," *EMBO J.*, 3:1671-1679, 1984.
Creissen et al., "Molecular characterization of glutathione reductase cDNAs from pea (*Pisum sativum* L.)," *Plant J.*, 2(1):129-131, 1992.
Creissen et al., "Simultaneous targeting of pea glutathione reductase and of a bacterial fusion protein to chloroplasts and mitochondria in transgenic tobacco," *Plant J.*, 8:167-175, 1995.
Gardiner et al., "Anchoring 9,371 maize expressed sequence tagged unigenes to the bacterial artificial chromosome contig map by two-dimensional overgo hybridization," *Plant Physiol.*, 134:1317-1326, 2004.
Gasser et al., "Structure, expression, and evolution of the 5-enolpyruvylshikimate-3-phosphate synthase genes of petunia and tomato," *J. Biol. Chem.*, 263:4280-4287, 1988.
GenBank Accession No. AY786443, Jun. 29, 2005.
GenBank Accession No. X53398, Oct. 5, 2005.
Herman et al., "A three-component dicamba O-demethylase from *Pseudomonas maltophilia*, strain DI-6: gene isolation, characterization, and heterologous expression," *J. Biol. Chem.*, 280(26):24759-24767, 2005.
Klee et al., "Cloning of an *Arabidopsis thaliana* gene encoding 5-enolpyruvylshikimate-3- phosphate synthase: sequence analysis and manipulation to obtain glyphosate-tolerant plants," *Mol. Gen. Genet.*, 210:437-442, 1987.
Mazur et al., "Sequence of a genomic DNA clone for the small subunit of ribulose bis-phosphate carboxylase-oxygenase from tobacco," *Nucleic Acids Res.*, 13(7):2373-2386, 1985.
Okagaki, "Nucleotide sequence of a long cDNA from the rice waxy gene," *Plant Mol. Biol.*, 19:513-516, 1992.
U.S. Appl. No. 12/440,173, filed Mar. 5, 2009, Bhatti et al.
"Banvel Herbicide," In: Crop Protection Reference, 11$^{th}$ Edition, pp. 1803-1821, 1995.
Al-Khatib et al., "Foliar absorption and translocation of dicamba from aqueous solution and dicamba-treated soil deposits," *Weed Technology*, 6:57-61, 1992.
Baker, "Response of cotton (gossypium hirsutum) to preplant-applied hormone-type herbicides," *Weed Technology*, 7:150-153, 1993.
Batie et al., "Phthalate dioxygenase reductase and related flavin-iron-sulfur containing electron transferases," In: Chemistry and Biochemistry of Flavoproteins, Muller (Ed.), CRC Press, Boca Raton, FL, pp. 543-556, 1992.
Batie et al., "Purification and characterization of phthalate oxygenase and phthalate oxygenase reductase from *Pseudomonas cepacia*," *J. of Bio. Chem.*, 262(4):1510-1518, 1987.
Bernhardt et al., "A 4-methoxybenzoate O-demethylase from *Pseudomonas putida*. A new type of monoxygenase system," *Eur. J. Biochem.*, 57(1):241-256, 1975.
Butler et al., "Structure-function analysis of the bacterial aromatic ring-hydroxylating dioxygenases," *Advances in Microbial Physiology*, 38:47-85, 1997.
Dehmel et al., "Cloning, nucleotide sequence and expression of the gene encoding a novel dioxygenase involved in metabolism of carboxydiphenyl ethers in *Pseudomonas pseudoalcaligenes* POB310," *Arch. Microbiol.*, 163:35-41, 1995.
Fogarty et al., "Microbiological degradation of the herbicide dicamba," *J. of Industrial Microbiology*, 14:365-370, 1995.
Fukumori et al., "Purification and characterization of 2,-dichlorophenoxyacetate/α-ketoglutarate dioxygenase," *J. Biol. Chem.*, 268:24311-24317, 1993.
Gibson et al., "Aromatic hydrocarbon dioxygenases in environmental biotechnology," *Current Opinion in Biotechnology*, 11:236-243, 2000.
Gurbiel et al., "Active site structure of Rieske-type prteins: electron nuclear double resonance studies of isotopically labeled phthalate dioxygenase from *Pseudomonas cepacia* and Rieske protein from rhodobacter capsulatus and molecular modeling studies of a Rieske center," *Biochemistry*, 35(24):7834-7845, 1996 (Abstract).
Krueger et al., "Use of dicamba-degrading microorganisms to protect dicamba susceptible plant species," *J. of Agri. and Food Chem.*, 39(5):1000-1003, 1991.
Magnusson et al., "Tolerance of soybean (glycine max) and sunflower (helianthus annuus) to fall-applied dicamba," *Weed Sci.*, 35:846-852, 1987.
Markus et al., "Purification and some properties of component A of the 4-chlorophenylacetate 3,4-dioxygenase from *Pseudomonas* species strain CBS," *J. of Biol. Chem.*, 261(27):12883-12888, 1986.
Mason et al., "The electron-transport proteins of hydroxylating bacterial dioxygenases," *Ann. Rev. of Microbiology*, 46:277-305, 1992.
Peniuk et al., "Physiological investigations into the resistance of a wild mustard (*Sinapis arvensis* L.) biotype to auxinic herbicides," *Weed Research*, 33:431-440, 1993.
Sarpe et al., "Researches on resistance of maize hybrids and inbred lines to the herbicides based on 2,4-D and dicamba," *Fragmenta Herbologica Jugoslavica*, 16(1-2):299-305, 1987.
Schroeder et al., "Soft red winter wheat (*Triticum aestivum*) response to dicamba and dicamba plus 2,4-D," *Weed Technology*, 3:67-71, 1989.
Wang et al., "A three-component enzyme system catalyzes the O demethylation of the herbicide dicamba in *Pseudomonas maltophilia* DI-6," *Applied and Environmental Microbiology*, 63(4):1623-1626, 1997.
Wang, "Characterization of cellular and enzymatic degradation of dicamba by *Pseudomonas maltophilia*, Strain DI-6," Thesis, University of Nebraska, Aug. 1996.
Office Action regarding U.S. Appl. No. 11/758,653 dated Dec. 29, 2009.
Office Action regarding U.S. Appl. No. 11/758,656 dated Sep. 15, 2009.
Response to Office Action regarding U.S. Appl. No. 11/758,656 dated Dec. 17, 2009.
Office Action regarding U.S. Appl. No. 11/758,657 dated Sep. 2, 2009.
Response to Office Action regarding U.S. Appl. No. 11/758,657 dated Jan. 4, 2010.
U.S. Appl. No. 60/811,276, filed Jun. 6, 2006, Feng et al.
"Banvel Herbicide" Product Insert, undated.
Behrens et al., "Dicamba resistance: enlarging and preserving biotechnology-based weed management strategies," *Science*, 316:1185-1188, 2007.
Buchanan-Wollaston, et al., Detoxification of the herbicide Dalapon by transformed plants, *J. Cell. Biochem.*, 13D, Abstract No. M503, p. 330, 1989.
Comai et al., "Expression in plants of a mutant *aroA* gene from *Salmonella typhimurium* confers tolerance to glyphosate," *Nature*, 317:741-744, 1985.
Cork et al., "Detection, isolation, and stability of megaplasmid-encoded chloroaromatic herbicide-degrading genes within *Pseudomonas* species," *Adv. Appl. Microbiol.*, 40:289-321, 1995.
Cork et al., "Microbial transformations of herbicides and pesticides," *Adv. Appl. Microbiology*, 36:1-67, 1991.
De Block et al., "Engineering herbicide resistance in plants by expression of a detoxifying enzyme," *EMBO J.*, 6(9):2513-2518, 1987.

Desvaux et al., "Genomic analysis of the protein secretion systems in *Clostridium acetobutylicum* ATCC 824," *Biochimica et Biophysica Acta*, 1745:223-253, 2005.

Hajdukiewicz et al., "The small, versatile pPZP family of agrobacterium binary vectors for plant transformation," *Plant Mol. Biol.*, 25:989-994, 1994.

Krueger et al., "Isolation and identification of microorganisms for the degradation of dicamba," *J. Agric. Food Chem.*, 37:534-538, 1989.

Misawa et al., "Expression of an *Erwinia phytoene* desaturase gene not only confers multiple resistance to herbicides interfering with carotenoid biosynthesis but also alters xanthophyll metabolism in transgenic plants," *Plant J.*, 6:481-489, 1994.

Padgette et al., "Development, identification and characterization of a glyphosate-tolerant soybean line," *Crop Sci.*, 35:1451-1461, 1995.

Sathasivan et al., "Nucleotide sequence of a mutant acetolactate synthase gene from an imidazolinone-resistant *Arabidopsis thaliana* var. Columbia," *Nucl. Acids Res.*, 18(8):2188, 1990.

Sprague, "Avoid herbicide spray tank contamination," *IPM News*, ipmnews.msu.edu/fieldcrop/tabid/56, Mar. 24, 2010.

Stalker et al., "Herbicide resistance in transgenic plants expressing a bacterial detoxification gene," *Science*, 242:419-423, 1988.

Streber et al., "Transgenic tobacco plants expressing a bacterial detoxifying enzyme are resistant to 2,4-D," *Bio/Technology*, 7:811-816, 1989.

Svab et al., "Aminoglycoside-3"-adenyltransferase confers resistance to spectinomycin and streptomycin in *Nicotiana tabacum*,"*Plant Mol. Biol.*, 14:197, 1990.

Thompson et al., "Soybean tolerance to early preplant applications of 2,4-D ester, 2,4-D amine, and dicamba," *Weed Technology*, 21:882-885, 2007.

Office Action regarding U.S. Appl. No. 10/330,662 dated Apr. 18, 2006.

Interview Summary regarding U.S. Appl. No. 10/330,662, dated Sep. 13, 2006.

Declaration of Donald P. Weeks regarding U.S. Appl. No. 10/330,662, dated Oct. 18, 2006.

Amendment and Response to Office Action regarding U.S. Appl. No. 10/330,662, dated Oct. 18, 2006.

Final Office Action regarding U.S. Appl. No. 10/330,662, dated Jan. 10, 2007.

Amendment and Response to Office Action regarding U.S. Appl. No. 10/330,662, dated Jul. 9, 2007.

Amendment regarding U.S. Appl. No. 10/330,662, dated Jul. 20, 2007.

Office Action regarding U.S. Appl. No. 10/330,662, dated Sep. 21, 2007.

Declaration of Donald P. Weeks regarding U.S. Appl. No. 10/330,662, dated Feb. 20, 2008.

Amendment and Response to Office Action regarding U.S. Appl. No. 10/330,662, dated Mar. 20, 2008.

Office Action regarding U.S. Appl. No. 10/330,662, dated Jul. 9, 2008.

Amendment and Remarks regarding U.S. Appl. No. 10/330,662, dated Jan. 9, 2009.

Final Office Action regarding U.S. Appl. No. 10/330,662, dated Apr. 24, 2009.

Amendment and Remarks regarding U.S. Appl. No. 10/330,662, dated Sep. 24, 2009.

Office Action regarding U.S. Appl. No. 10/330,662, dated Jan. 11, 2010.

Interview Summary regarding U.S. Appl. No. 10/330,662, dated Mar. 19, 2010.

Amendment and Remarks regarding U.S. Appl. No. 10/330,662, dated May 4, 2010.

Notice of Allowance Regarding U.S. Appl. No. 10/330,662, dated Jul. 12, 2010.

Amendment and Response to Office Action regarding U.S. Appl. No. 11/758,653, dated Mar. 29, 2010.

Final Office Action regarding U.S. Appl. No. 11/758,653, dated Jun. 24, 2010.

Final Office Action regarding U.S. Appl. No. 11/758,656, dated Apr. 14, 2010.

Final Office Action regarding U.S. Appl. No. 11/758,657, dated Apr. 14, 2010.

Response to Final Office Action regarding U.S. Appl. No. 11/758,657, dated Jul. 14, 2010.

Office Action regarding U.S. Appl. No. 11/758,660, dated Apr. 28, 2010.

Amendment and Response to Final Office Action regarding U.S. Appl. No. 11/758,653, dated Aug. 16, 2010.

Declaration of Yuechun Wan Under 37 C.F.R. §1.132, dated Aug. 11, 2010.

Amendment and Response to Final Office Action regarding U.S. Appl. No. 11/758,656, dated Aug. 16, 2010.

Notice of Allowance regarding U.S. Appl. No. 11/758,656, dated Oct. 4, 2010.

Notice of Allowance regarding U.S. Appl. No. 11/758,657, dated Sep. 10, 2010.

Response to Official Action regarding U.S. Appl. No. 11/758,660, dated Sep. 27, 2010.

Notice of Allowance regarding U.S. Appl. No. 11/758,653, dated Oct. 5, 2010.

U.S. Appl. No. 12/875,747, filed Sep. 3, 2010, Weeks et al.

\* cited by examiner

|   | Construct Name | Promoter | CTP | DMO | 3'UTR |
|---|---|---|---|---|---|
| 1 | WT control | None | None | None | None |
| 2 | pMON68933 | PClSV | PsRbcS with extra 27 amino acids | DMOc-nat | RbcS2-E9 |
| 3 | pMON73690 | FMV | None | DMOc-dc | RbcS2-E9 |
| 4 | pMON73696 | FMV | AtRbcS (CTP1) | DMOw-dc | RbcS2-E9 |
| 5 | pMON73697 | FMV | None | DMOw-dc | RbcS2-E9 |
| 6 | pMON73698 | FMV | AtRbcS (CTP1) | DMOc-dc | RbcS2-E9 |

CHLOROPLAST TRANSIT PEPTIDES FOR EFFICIENT TARGETING OF DMO AND USES THEREOF

This application claims the priority of U.S. Provisional Patent Application 60/891,675, filed Feb. 26, 2007, the disclosure of which is incorporated herein by reference in its entirety.

BACKGROUND OF THE INVENTION

1. Field of the Invention

The invention relates to the field of plant biotechnology. More particularly, the invention relates to identification and use of chloroplast transit peptides allowing efficient processing and localization of dicamba monooxygenase enzymes in plants.

2. Description of the Related Art

DMO (dicamba monooxygenase) catalyzes the degradation of the herbicide dicamba (3,6-dichloro-o-anisic acid) to non-toxic 3,6-dichlorosalicylic acid (3,6-DCSA) in plants, thus conferring herbicide tolerance. Activity of DMO requires two intermediary proteins for shuttling electrons from NADH to dicamba, a reductase and a ferredoxin (U.S. Pat. No. 7,022,896; Herman et al., 2005). However dicamba tolerance in transgenic plants has been demonstrated through transformation with DMO alone, indicating that a plant's endogenous reductase and ferredoxin may substitute in shuttling the electrons. The plant ferredoxin that is involved in electron transfer is localized in the plastids. Thus, in order to obtain efficient performance of DMO and thus improved tolerance to dicamba, there is a need for targeting the DMO to chloroplasts.

In many cases, this targeting may be achieved by the presence of an N-terminal extension, called a chloroplast transit peptide (CTP) or plastid transit peptide. Chromosomal transgenes from bacterial sources must have a sequence encoding a CTP sequence fused to a sequence encoding an expressed polypeptide if the expressed polypeptide is to be compartmentalized in the plant plastid (e.g. chloroplast). Accordingly, localization of an exogenous polypeptide to a chloroplast is often accomplished by means of operably linking a polynucleotide sequence encoding a CTP sequence to the 5' region of a polynucleotide encoding the exogenous polypeptide. The CTP is removed in a processing step during translocation into the plastid. Processing efficiency may, however, be affected by the amino acid sequence of the CTP and nearby sequences at the $NH_2$ terminus of the peptide.

Weeks et al. (U.S. Pat. No. 7,022,896) describe potential use of a maize cab-m7 signal sequence (see Becker et al., 1992 and PCT WO 97/41228; GenBank Accession No. X53398) and a pea glutathione reductase signal sequence (Creissen et al., 1992 and PCT WO 97/41228) in targeting DMO to plant plastids, but no data on efficiency of processing or targeting is given. A pea Rubisco small subunit (RbcS) CTP including a 27 aa sequence including coding sequence for pea Rubisco enzyme small subunit has also been used to target DMO to chloroplasts (e.g. U.S. Prov. Appl. Ser. No. 60/811,152). However, it has been found during Western blot analysis that this pea RbcS CTP generates a correctly processed DMO protein band (~38 kDa), but also a larger band (~41 kDa) corresponding to that of DMO and the 27 aa of RbcS coding region. The extra amino acids could impact the DMO activity adversely. In addition, additional proteins in a transgenic product due to incomplete processing of DMO create regulatory hurdles and require additional efforts in characterization of the product for the purposes of product registration by government agencies thereby raising the cost of product registration. Thus, there is a need for identifying CTPs that efficiently generate correctly processed DMO, thereby providing the advantage of full DMO activity as well as ease of product characterization.

SUMMARY OF THE INVENTION

One aspect of the invention relates to a recombinant DNA molecule comprising a nucleotide sequence encoding a chloroplast transit peptide operably linked to a nucleotide sequence encoding dicamba monooxygenase, wherein the nucleotide sequence encodes a chloroplast transit peptide comprising a sequence selected from the group consisting of SEQ ID NOs: 1-11. In certain embodiments, the recombinant DNA molecule comprises a nucleotide sequence selected from the group consisting of SEQ ID NOs: 12-22. In certain embodiments, the recombinant DNA molecule comprises a nucleotide sequence encoding dicamba monooxygenase selected from the group consisting of SEQ ID NOs: 24, 26, 28, 30, 32, 34, 36, 38, and 40. A DNA construct comprising the DNA molecule operably linked to a promoter which is functional in a plant cell is also an aspect of the invention.

In another aspect, the invention comprises a plant cell transformed with a DNA molecule comprising a nucleotide sequence encoding a chloroplast transit peptide operably linked to a nucleotide sequence encoding dicamba monooxygenase, wherein the sequence of the chloroplast transit peptide is selected from the group consisting of SEQ ID NOs: 1-11. In certain embodiments, the recombinant DNA molecule comprises a nucleotide sequence selected from the group consisting of SEQ ID NOs: 12-22. In certain embodiments, the DNA molecule comprises a nucleotide sequence encoding a dicamba monooxygenase selected from the group consisting of SEQ ID NOs: 24, 26, 28, 30, 32, 34, 36, 38, and 40, wherein the DNA molecule is operably linked to a promoter which is functional in a plant cell. In particular embodiments the DNA molecule comprises a nucleotide sequence selected from the group consisting of SEQ ID NOs: 23, 25, 27, 29, 31, 33, 35, 37, and 39.

In certain embodiments, the plant cell is a dicotyledonous plant cell. In other embodiments, the plant cell is a monocotyledonous plant cell. In particular embodiments, the plant cell is a soybean, cotton, maize, or rapeseed plant cell. The invention also relates to a plant tissue culture comprising such a cell, and to a transgenic seed and to a transgenic plant comprising such cells. In certain embodiments, the transgenic seed or plant is a dicotyledonous seed or plant. In other embodiments, the transgenic seed or plant is a monocotyledonous seed or plant. The transgenic seed or plant may be a soybean, cotton, maize or rapeseed seed or plant.

The invention further relates to a method for producing a dicamba tolerant plant comprising: introducing a recombinant DNA molecule comprising a nucleotide sequence encoding a chloroplast transit peptide operably linked to a nucleotide sequence encoding dicamba monooxygenase, wherein the nucleotide sequence encoding the chloroplast transit peptide is selected from the group consisting of SEQ ID NOs: 12-22, into a plant cell, and regenerating a plant therefrom. In certain embodiments, the recombinant DNA molecule comprises a nucleotide sequence encoding dicamba monooxygenase which is selected from the group consisting of SEQ ID NOs: 24, 26, 28, 30, 32, 34, 36, 38, and 40. The DNA molecule may be operably linked to a promoter which is functional in a plant cell. The method may further comprise producing a dicamba tolerant plant by crossing a parent plant with itself or with a second plant, wherein the parent plant and/or the second plant comprises the DNA construct and the dicamba tolerant plant inherits the DNA construct from said parent plant and/or the second plant.

A method for expressing dicamba monooxygenase in a plant cell comprising operably linking a selected CTP to a sequence encoding dicamba monooxygenase is a further aspect of the invention.

In another aspect, the invention relates to a method for controlling weed growth in a crop growing environment, comprising: growing such a plant or a seed thereof, and applying to the crop growing environment an amount of dicamba herbicide effective to control weed growth. The dicamba herbicide may be applied over the top to the crop growing environment, whereby the amount of dicamba herbicide does not damage said plant of or seed thereof and damages a plant or seed of the same genotype as such a plant or seed but lacking the construct.

A further aspect of the invention relates to a method for producing food, feed, or an industrial product comprising:
 a) obtaining a plant comprising a nucleotide sequence encoding a promoter functional in a plant cell operably linked in the 5' to 3' direction to a nucleotide sequence encoding a chloroplast transit peptide and a nucleotide sequence encoding dicamba monooxygenase, or a part thereof;
 b) preparing the food, feed, fiber, or industrial product from the plant or part thereof.

In certain embodiments of the method, the food or feed is grain, meal, oil, starch, flour, or protein. In other embodiments of the method, the industrial product is biofuel, fiber, industrial chemicals, a pharmaceutical, or nutraceutical.

A dicamba tolerant seed for providing protection against pre emergence application of dicamba comprising a DNA encoding chloroplast transit peptide operably linked to a DNA encoding dicamba monooxygenase is a further aspect of the invention. In certain embodiments, the dicamba tolerant seed comprises a nucleotide sequence encoding a chloroplast transit peptide, such as a nucleotide sequence selected from the group consisting of SEQ ID NO: 12-22. The dicamba tolerant seed may further comprise a nucleotide sequence encoding dicamba monooxygenase selected from the group consisting of SEQ ID NOS: 24, 26, 28, 30, 32, 34, 36, 38, and 40.

Another aspect of the invention relates to a method for improving the standability of a monocot plant comprising: a) obtaining and growing a plant produced by crossing a parent plant with itself or with a second plant, wherein the parent plant and/or the second plant comprises the DNA construct and the dicamba tolerant plant inherits the DNA construct from said parent plant and/or the second plant; and b) treating the plant with dicamba. In certain embodiments, the plant is a corn plant. In yet other embodiments, standability-related parameters including brace root shape, number, length, and/or structure; percent lodging; and yield may be measured.

DETAILED DESCRIPTION OF THE INVENTION

Figure 1:
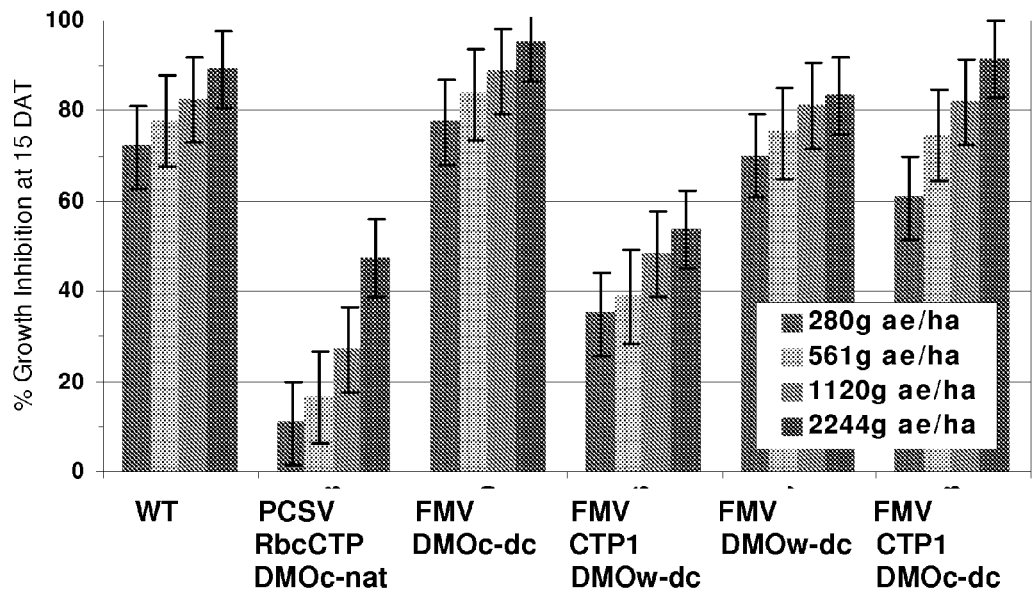
FIG. 1 Use of CTP-DMO constructs for proper processing of DMO and provision of dicamba tolerance.

In accordance with the invention, compositions and methods are provided for expressing and transporting dicamba monooxygenase (DMO) polypeptides with increased efficiency to chloroplasts in plant cells. The compositions and methods of the invention will therefore find use in increasing the tolerance of plants and cells to the herbicide dicamba. By targeting DMO to chloroplasts with a chloroplast transit peptide (CTP) in particular, improved DMO expression and tolerance to dicamba may be achieved.

Surprisingly, however, the present inventors have discovered that certain CTPs do not function well in combination with DMO. For example, some CTPs do not result in adequate protein expression. This can include incorrect expression of the protein, with the production of proteins of altered size and incomplete activity in vivo. This can result in incomplete herbicide tolerance and complicate regulatory approval. The present invention provides CTPs that, when used in combination with DMO, provide unexpected benefits including, but not necessarily limited to, improved levels of transport to the chloroplast, increased herbicide tolerance in DMO-expressing transgenic plants, desired levels of protein expression of the correct size, and appropriate post-translational modifications. One such example of a CTP providing unexpected benefits when in combination with DMO is the transit peptide CTP2, including the nucleic acids of SEQ ID NO:15 or 16, and including sequences encoding SEQ ID NOs:4 or 5. In other embodiments, a pea (*Pisum sativum*) Rubisco small subunit CTP coding sequence is used, such as represented by SEQ ID NO: 13 or encoding SEQ ID NO: 2. A DNA construct comprising a DMO coding sequence operably linked to a CTP2 and/or pea Rubisco small subunit CTP transit peptide coding sequence thus forms one aspect of the invention, as does a protein encoded thereby.

Dicamba monooxygenase of *Pseudomonas maltophilia* strain DI6 (Herman et al., 2005; U.S. Patent Publication 20030115626; GenBank accession AY786443, the DMO-encoding sequence of which is herein incorporated by reference) catalyzes the detoxification of the herbicide dicamba. DMO is part of a 3-component system for detoxification of dicamba to the non-toxic 3,6-dichlorosalicylic acid (3,6-DCSA), and as noted above requires reductase and ferredoxin functions for transfer of electrons. Since the endogenous plant ferredoxin that is involved in electron transfer is localized in the plastids, in order to obtain efficient activity of DMO and thus tolerance such as in dicots or improved tolerance such as in monocots to dicamba, DMO is preferably targeted to plastids (e.g. chloroplasts).

Chloroplast transit peptides (CTPs) were tested for efficiency in allowing targeting and processing of DMO to plastids. Plastid localization and processing of the DMO in connection with these CTPs ranged from none, or partial, to complete. Only some of the CTPs were found to allow complete processing of DMO to a correct size. The ability of any given CTP to provide for complete and efficient processing of DMO was therefore unpredictable and surprising based on its protein or nucleotide sequences.

Further, it has also been found in *Arabidopsis* that without a proper CTP, there is little or no expression of DMO correlating with little or no tolerance to dicamba. This suggests that chloroplast targeting is important for dicamba detoxification and hence tolerance. CTPs that allow efficient processing of DMO will be useful in targeting DMO to plastids, such as chloroplasts, of crop plants thereby providing the advantage of full DMO activity and higher tolerance to dicamba as well as ease of product characterization and reduced cost of registration.

Chimeric DNA molecules comprising a DNA encoding a chloroplast transit peptide operably linked to a DNA encoding dicamba monooxygenase can be prepared by molecular biological methods known to those skilled in this art (e.g. Sambrook et al., 1989). CTPs operably linked to known DNA molecules encoding DMO, including those identified in Table 1, are provided by the invention for the improved expression of DMO in plants.

A chloroplast transit peptide from any gene that is encoded in the nucleus and the product of which targets a polypeptide to the chloroplast can be tested for efficient expression of DMO. Chloroplast transit peptide sequences can be isolated or synthesized. The nucleotide sequence encoding a CTP may be optimized for expression in dicots, monocots, or both. The following transit peptides were tested by operably linking each to a DMO coding sequence: PsRbcS-derived CTPs (SEQ ID NO:1 and 2: *Pisum sativum* Rubisco small subunit CTP; Coruzzi et al., 1984); AtRbcS CTP (SEQ ID NO:3: *Arabidopsis thaliana* Rubisco small subunit 1A CTP; CTP1; U.S. Pat. No. 5,728,925); AtShkG CTP (SEQ ID NO:4: *Arabidopsis thaliana* 5-enolpyruvylshikimate-3-phosphate synthase (EPSPS); CTP2; Klee et al., 1987); AtShkGZm CTP (SEQ ID NO:5: CTP2synthetic; codon optimized for monocot expression; SEQ ID NO:14 of WO04009761); PhShkG CTP (SEQ ID NO:6: *Petunia hybrida* EPSPS; CTP4; codon optimized for monocot expression; Gasser et al., 1988); TaWaxy CTP (SEQ ID NO:7: *Triticum aestivum* granule-bound starch synthase CTPsynthetic, codon optimized for corn expression: Clark et al., 1991); OsWaxy CTP (SEQ ID NO:8: *Oryza sativa* starch synthase CTP; Okagaki, 1992); NtRbcS CTP (SEQ ID NO: 9: *Nicotiana tabacum* ribulose 1,5-bisphosphate carboxylase small subunit chloroplast transit peptide; Mazur, et al., 1985); ZmAS CTP (SEQ ID NO:10: *Zea mays* anthranilate synthase alpha 2 subunit gene CTP; Gardiner et al., 2004); and RgAS CTP (SEQ ID NO:11: *Ruta graveolens* anthranilate synthase CTP; Bohlmann, et al., 1995). The nucleotide sequences coding for SEQ ID NO:1-SEQ ID NO:11 are given in SEQ ID NO:12-SEQ ID NO:22, respectively.

Other transit peptides that may be useful include maize cab-m7 signal sequence (Becker et al., 1992; PCT WO 97/41228) and the pea (*Pisum sativum*) glutathione reductase signal sequence (Creissen et al., 1995; PCT WO 97/41228). CTPs with additional amino acids derived from the coding region of the gene they are part of or are fused to, such as AtRbcS CTP which includes the transit peptide, 24 amino acids of the mature Rubisco protein, and then a repeat of the last 6 amino acids of the transit peptide, can be utilized for producing DMO. ZmAS CTP also contain additional 18 amino acids derived from the coding region of the gene. Other CTPs with additional amino acids (for example 27 amino acids) derived from the coding region of the gene they are part of, such as PsRbcS CTP, followed by amino acids introduced by cloning methods (for example 3 amino acids) can also be utilized for producing DMO. CTPs with fewer amino acids (for example 21 amino acids) coding for a full length CTP such as RgAs CTP can also be utilized for producing DMO. Preferably, a nucleic acid sequence coding for a full length CTP is utilized. One or more nucleotide additions or deletions may be included to facilitate cloning of a CTP. These additions or deletions may be after or before other expression elements and coding regions, resulting in modification of one or more encoded amino acids, for instance at or near a restriction enzyme recognition site.

In one embodiment, the invention relates to a nucleic acid sequence encoding a chloroplast transit peptide that has at least 70% identity to a polypeptide sequence of any one or more of SEQ ID NOs: 1-11, including at least about 75%, 80%, 85%, 90%, 95%, 97%, 98%, 99% and greater sequence identity to these sequences, including 100% identity. In particular embodiments, the nucleic acid sequence encodes a chloroplast transit peptide identical to one of SEQ ID NOs: 1-11. In another embodiment, the nucleic acid coding for the CTP has at least 70% sequence identity to a nucleic acid sequence of any one or more of SEQ ID NOs:12-22, including at least about 75%, 80%, 85%, 90%, 95%, 97%, 98%, 99% and greater sequence identity, including 100% identity, to one or more of these sequences. Polypeptide or polynucleotide comparisons of these and any other sequence as described herein may be carried out and identity determined as is well known in the art, for example, using MEGAlign (DNAStar, Inc., 1228 S. Park St., Madison, Wis.) with default parameters. Such software matches similar sequences by assigning degrees of similarity or identity.

DMO can be targeted to other organelles such as mitochondria by using pre-sequences to make use of the ferrodoxin redox system present in this organelle. Alternatively, DMO can be targeted to both chloroplast and mitochondria by a dual-targeting peptide to make use of two ferrodoxin redox systems to work even more effectively. Such elements are known to those skilled in the art. For example, mitochondrial pre-sequences are described in Silva Filho et al., (1996). Nucleic acid sequences that encode dual-targeting peptide sequences can be identified from the nucleic acids coding for the following proteins which are known be targeted to both chloroplasts and mitochondria: Zn-MP (Moberg et al., 2003), gluthathione reductase (Rudhe et al., 2002; Creissen et al., 1995) and histdyl-tRNA synthetase (Akashi et al., 1998). Examples of DMO-encoding sequences that may be used in this regard are found, for example, in the sequences encoding the polypeptides of SEQ ID NOs 24, 26, 28, 30, 32, 34, 36, 38, 40, as shown in Table 1.

TABLE 1

DMO and DMO variants utilized.

| DMO/or variant | PRT SEQ ID | DNA SEQ ID | PRT Length | Predicted aa at position 2 | Predicted aa at position 3 | Predicted aa at position 112 | Codon usage |
|---|---|---|---|---|---|---|---|
| DMO-Cat(A) | 24 | 23 | 340 | Ala | Thr | Cys | dicot |
| DMO-Cat(L) | 26 | 25 | 340 | Leu | Thr | Cys | dicot |
| DMO-Wat(L) | 28 | 27 | 340 | Leu | Thr | Trp | dicot |
| DMO-Cnat(A) | 30 | 29 | 340 | Ala | Thr | Cys | bacteria |
| DMO-Wat(A) | 32 | 31 | 340 | Ala | Thr | Trp | dicot |

TABLE 1-continued

DMO and DMO variants utilized.

| DMO/or variant | PRT SEQ ID | DNA SEQ ID | PRT Length | Predicted aa at position 2 | Predicted aa at position 3 | Predicted aa at position 112 | Codon usage |
|---|---|---|---|---|---|---|---|
| DMO-Wnat(T) | 34 | 33 | 339 | Thr | Phe | Trp (at 111) | bacterium |
| DMO-Cnat(L) | 36 | 35 | 340 | Leu | Thr | Cys | bacterium |
| DMO-Wmc(L) | 38 | 37 | 340 | Leu | Thr | Trp | monocot |
| DMO-Wmc(A) | 40 | 39 | 340 | Ala | Thr | Trp | monocot |

In some embodiments, the nucleic acid encoding a dicamba monooxygenase has at least 70% identity to a sequence that encodes a polypeptide of any of SEQ ID NOs: 24, 26, 28, 30, 32, 34, 36, 38, or 40, including at least about 75%, 80%, 85%, 90%, 95%, 97%, 98%, 99% and greater sequence identity to these sequences. In certain embodiments, the nucleic acid has at least 70% sequence identity to a nucleic acid sequence of any of SEQ ID NOs: 23, 25, 27, 29, 31, 33, 35, 37, or 39, including at least about 75%, 80%, 85%, 90%, 95%, 97%, 98%, 99%, and greater sequence identity to one of these sequences. In further embodiments, a dicamba monooxygenase may be a variant of any such sequences and/or may be a synthetic DMO molecule engineered, for example, as described in U.S. Prov. Appl. Ser. No. 60/884, 854, filed Jan. 12, 2007, entitled "DMO Methods And Compositions," the entire disclosure of which is specifically incorporated herein by reference.

Variants of DMOs having a capability to degrade auxin-like herbicides, as well as glyphosate or other herbicide tolerance genes can readily be prepared and assayed for activity according to standard methods. Such sequences can also be identified by techniques known in the art, for example, from suitable organisms including bacteria that degrade auxin-like herbicides, such as dicamba, or other herbicides (U.S. Pat. No. 5,445,962; Cork and Krueger, 1991; Cork and Khalil, 1995). One means of isolating a DMO or other sequence is by nucleic acid hybridization, for example, to a library constructed from the source organism, or by RT-PCR using mRNA from the source organism and primers based on the disclosed desaturases. The invention therefore encompasses use of nucleic acids hybridizing under stringent conditions to a DMO encoding sequence described herein. One of skill in the art understands that conditions may be rendered less stringent by increasing salt concentration and decreasing temperature. Thus, hybridization conditions can be readily manipulated, and thus will generally be a method of choice depending on the desired results. An example of high stringency conditions is 5×SSC, 50% formamide and 42° C. By conducting a wash under such conditions, for example, for 10 minutes, those sequences not hybridizing to a particular target sequence under these conditions can be removed.

Variants can also be chemically synthesized, for example, using the known DMO polynucleotide sequences according to techniques well known in the art. For instance, DNA sequences may be synthesized by phosphoroamidite chemistry in an automated DNA synthesizer. Chemical synthesis has a number of advantages. In particular, chemical synthesis is desirable because codons preferred by the host in which the DNA sequence will be expressed may be used to optimize expression. Not all of the codons need to be altered to obtain improved expression, but preferably at least the codons rarely used in the host are changed to host-preferred codons. High levels of expression can be obtained by changing greater than about 50%, most preferably at least about 80%, of the codons to host-preferred codons. The codon preferences of many host cells are known (e.g. PCT WO 97/31115; PCT WO 97/11086; EP 646643; EP 553494; and U.S. Pat. Nos. 5,689, 052; 5,567,862; 5,567,600; 5,552,299 and 5,017,692). The codon preferences of other host cells can be deduced by methods known in the art. Also, using chemical synthesis, the sequence of the DNA molecule or its encoded protein can be readily changed to, for example, optimize expression (for example, eliminate mRNA secondary structures that interfere with transcription or translation), add unique restriction sites at convenient points, and delete protease cleavage sites.

Modification and changes may be made to the polypeptide sequence of a protein such as the DMO sequences provided herein while retaining or modifying enzymatic activity as desired. Illustrative methods for generating DMO sequences are provided in U.S. Prov. Appl. Ser. No. 60/884,854, filed Jan. 12, 2007. The following is a discussion based upon changing the amino acids of a protein to create an equivalent, or even an improved, modified polypeptide and corresponding coding sequences. It is known, for example, that certain amino acids may be substituted for other amino acids in a protein structure without appreciable loss of interactive binding capacity with structures such as binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the DMO peptide sequences described herein or other herbicide tolerance polypeptides and corresponding DNA coding sequences without appreciable loss of their biological utility or activity.

In making such changes, the hydropathic index of amino acids may be considered. The importance of the hydropathic amino acid index in conferring interactive biologic function on a protein is generally understood in the art (Kyte et al., 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics (Kyte et al., 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101 states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent protein. In such changes, the substitution of amino acids whose hydrophilicity values are within ±2 is preferred, those which are within ±1 are particularly preferred, and those within ±0.5 are even more particularly preferred. Exemplary substitutions which take these and various of the foregoing characteristics into consideration are well known to those of skill in the art and include: arginine and lysine; glutamate and aspartate; serine and threonine; glutamine and asparagine; and valine, leucine and isoleucine.

A DNA construct comprising a CTP sequence operably linked to a DMO sequence can be expressed in test system such as protoplasts, transiently or stably transformed plant cells by operably linked them to a promoter functional in plants. Examples describing such promoters include U.S. Pat. No. 6,437,217 (maize RS81 promoter), U.S. Pat. No. 5,641,876 (rice actin promoter; OsAct1), U.S. Pat. No. 6,426,446 (maize RS324 promoter), U.S. Pat. No. 6,429,362 (maize PR-1 promoter), U.S. Pat. No. 6,232,526 (maize A3 promoter), U.S. Pat. No. 6,177,611 (constitutive maize promoters), U.S. Pat. Nos. 5,322,938, 5,352,605, 5,359,142 and 5,530,196 (35S promoter), U.S. Pat. No. 6,433,252 (maize L3 oleosin promoter), U.S. Pat. No. 6,429,357 (rice actin 2 promoter as well as a rice actin 2 intron), U.S. Pat. No. 5,837,848 (root specific promoter), U.S. Pat. No. 6,294,714 (light inducible promoters), U.S. Pat. No. 6,140,078 (salt inducible promoters), U.S. Pat. No. 6,252,138 (pathogen inducible promoters), U.S. Pat. No. 6,175,060 (phosphorus deficiency inducible promoters), U.S. Pat. No. 6,388,170 (e.g. PClSV promoter), the PClSV promoter of SEQ ID NO:41, U.S. Pat. No. 6,635,806 (gamma-coixin promoter), and U.S. Pat. No. 7,151,204 (maize chloroplast aldolase promoter). Additional promoters that may find use are a nopaline synthase (NOS) promoter (Ebert et al., 1987), the octopine synthase (OCS) promoter (which is carried on tumor-inducing plasmids of *Agrobacterium tumefaciens*), the caulimovirus promoters such as the cauliflower mosaic virus (CaMV) 19S promoter (Lawton et al., 1987), the CaMV 35S promoter (Odell et al., 1985), the figwort mosaic virus 35S-promoter (Walker et al., 1987), the sucrose synthase promoter (Yang et al., 1990), the R gene complex promoter (Chandler et al., 1989), and the chlorophyll a/b binding protein gene promoter, etc. In the present invention, CaMV35S with enhancer sequences (e35S; U.S. Pat. Nos. 5,322,938; 5,352,605; 5,359,142; and 5,530,196), FMV35S (U.S. Pat. Nos. 6,051,753; 5,378,619), peanut chlorotic streak caulimovirus (PClSV; U.S. Pat. No. 5,850,019), At.Act 7 (Accession # U27811), At.ANT1 (US Patent Application 20060236420), FMV.35S-EF1a (US Patent Application 20050022261), eIF4A10 (Accession # X79008) and AGRtu.nos (GenBank Accession V00087; Depicker et al, 1982; Bevan et al., 1983), rice cytosolic triose phosphate isomerase (OsTPI; U.S. Pat. No. 7,132,528), and rice actin 15 gene (OsAct15; U.S. Patent Application 2006-0162010) promoters may be of particular benefit.

A 5' UTR that functions as a translation leader sequence is a DNA genetic element located between the promoter sequence of a gene and the coding sequence may be included between a promoter and CTP-DMO sequence. The translation leader sequence is present in the fully processed mRNA upstream of the translation start sequence. The translation leader sequence may affect processing of the primary transcript to mRNA, mRNA stability or translation efficiency. Examples of translation leader sequences include maize and petunia heat shock protein leaders (U.S. Pat. No. 5,362,865), plant virus coat protein leaders, plant rubisco leaders, GmHsp (U.S. Pat. No. 5,659,122), PhDnaK (U.S. Pat. No. 5,362,865), AtAnt1, TEV (Carrington and Freed, 1990), and AGRtunos (GenBank Accession V00087; Bevan et al., 1983) among others. (Turner and Foster, 1995). In the present invention, 5' UTRs that may in particular find benefit are GmHsp (U.S. Pat. No. 5,659,122), PhDnaK (U.S. Pat. No. 5,362,865), AtAnt1, TEV (Carrington and Freed, 1990), OsAct1 (U.S. Pat. No. 5,641,876), OsTPI (U.S. Pat. No. 7,132,528), OsAct15 (US Publication No. 20060162010), and AGRtunos (GenBank Accession V00087; Bevan et al., 1983).

The 3' non-translated sequence, 3' transcription termination region, or poly adenylation region means a DNA molecule linked to and located downstream of a structural polynucleotide molecule and includes polynucleotides that provide polyadenylation signal and other regulatory signals capable of affecting transcription, mRNA processing or gene expression. The polyadenylation signal functions in plants to cause the addition of polyadenylate nucleotides to the 3' end of the mRNA precursor. The polyadenylation sequence can be derived from the natural gene, from a variety of plant genes, or from T-DNA genes. These sequences may be included downstream of a CTP-DMO sequence. An example of a 3' transcription termination region is the nopaline synthase 3' region (nos 3'; Fraley et al., 1983). The use of different 3' nontranslated regions is exemplified (Ingelbrecht et al., 1989). Polyadenylation molecules from a *Pisum sativum* RbcS2 gene (Ps.RbcS2-E9; Coruzzi et al., 1984), AGRtu.nos (Genbank Accession E01312), E6 (Accession # U30508), and TaHsp17 (wheat low molecular weight heat shock protein gene; Accession # X13431) in particular may be of benefit for use with the invention.

In addition to expression elements described above, an intron may be required in between a promoter and a 3' UTR for expressing a coding region, especially in monocots. An "intron" refers to a polynucleotide molecule that may be isolated or identified from the intervening sequence of a genomic copy of a gene and may be defined generally as a region spliced out during mRNA processing prior to translation. Alternately, introns may be synthetically produced.

Introns may themselves contain sub-elements such as cis-elements or enhancer domains that effect the transcription of operably linked genes. A "plant intron" is a native or non-native intron that is functional in plant cells. A plant intron may be used as a regulatory element for modulating expression of an operably linked gene or genes. A polynucleotide molecule sequence in a transformation construct may comprise introns. The introns may be heterologous with respect to the transcribable polynucleotide molecule sequence. Examples of introns include the corn actin intron (U.S. Pat. No. 5,641,876), the corn HSP70 intron (ZmHSP70; U.S. Pat. No. 5,859,347; U.S. Pat. No. 5,424,412), and rice TPI intron (OsTPI; U.S. Pat. No. 7,132,528) and are of benefit in practicing this invention.

The CTP-DMO constructs can be tested for providing proper processing of DMO in a test system such as protoplasts, or transiently or stably transformed plant cells of monocots or dicots by methods known to those skilled in the art of plant tissue culture and transformation. Any of the techniques known in the art for introduction of transgene constructs into plants may be used in accordance with the invention (see, for example, Miki et al., 1993). Suitable methods for transformation of plants are believed to include virtually any method by which DNA can be introduced into a cell, such as by electroporation as illustrated in U.S. Pat. No. 5,384,253; microprojectile bombardment as illustrated in U.S. Pat. Nos. 5,015,580; 5,550,318; 5,538,880; 6,160,208; 6,399,861; and 6,403,865; *Agrobacterium*-mediated transformation as illustrated in U.S. Pat. Nos. 5,635,055; 5,824,877; 5,591,616; 5,981,840; and 6,384,301; and protoplast transformation as illustrated in U.S. Pat. No. 5,508,184. Through the application of techniques such as these, the cells of virtually any plant species may be stably transformed, and these cells may be developed into transgenic plants. Techniques that may be particularly useful in the context of cotton transformation are disclosed in U.S. Pat. Nos. 5,846,797, 5,159,135, 5,004,863, and 6,624,344. Techniques for transforming *Brassica* plants in particular are disclosed, for example, in U.S. Pat. No. 5,750,871; and techniques for transforming soybean are disclosed in, for example, Zhang et al., 1999, U.S. Pat. No. 6,384,301, and U.S. Pat. No. 7,002,058. Techniques for transforming corn are disclosed in WO9506722. Some non-limiting examples of plants that may find use with the invention include alfalfa, barley, beans, beet, broccoli, cabbage, carrot, canola, cauliflower, celery, Chinese cabbage, corn, cotton, cucumber, dry bean, eggplant, fennel, garden beans, gourd, leek, lettuce, melon, oat, okra, onion, pea, pepper, pumpkin, peanut, potato, pumpkin, radish, rice, sorghum, soybean, spinach, squash, sweet corn, sugarbeet, sunflower, tomato, watermelon, and wheat.

After effecting delivery of exogenous DNA to recipient cells, the next steps in generating transgenic plants generally concern identifying the transformed cells for further culturing and plant regeneration. In order to improve the ability to identify transformants, one may desire to employ a selectable or screenable marker gene with a transformation vector prepared in accordance with the invention. In this case, one would then generally assay the potentially transformed cell population by exposing the cells to a selective agent or agents, or one would screen the cells for the desired marker gene trait.

Cells that survive the exposure to the selective agent, or cells that have been scored positive in a screening assay, may be cultured in media that supports regeneration of plants. Any suitable plant tissue culture media, for example, MS or N6 media (Murashige and Skoog, 1962; Chu et al., 1975); may be modified by including further substances such as growth regulators. Tissue may be maintained on a basic media with growth regulators until sufficient tissue is available to begin plant regeneration efforts, or following repeated rounds of manual selection, until the morphology of the tissue is suitable for regeneration, typically at least 2 weeks, then transferred to media conducive to shoot formation. Cultures are transferred periodically until sufficient shoot formation had occurred. Once shoot are formed, they are transferred to media conducive to root formation. Once sufficient roots are formed, plants can be transferred to soil for further growth and maturity.

To confirm the presence of the exogenous DNA or "transgene(s)" in the regenerating plants, a variety of assays may be performed. Such assays include, for example, "molecular biological" assays, such as Southern and northern blotting and PCR™; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

Once a transgene has been introduced into a plant, that gene can be introduced into any plant sexually compatible with the first plant by crossing, without the need for ever directly transforming the second plant. Therefore, as used herein the term "progeny" denotes the offspring of any generation of a parent plant prepared in accordance with the instant invention, wherein the progeny comprises a selected DNA construct prepared in accordance with the invention. A "transgenic plant" may thus be of any generation. "Crossing" a plant to provide a plant line having one or more added transgenes or alleles relative to a starting plant line, as disclosed herein, is defined as the techniques that result in a particular sequence being introduced into a plant line by crossing a starting line with a donor plant line that comprises a transgene or allele of the invention. To achieve this one could, for example, perform the following steps: (a) plant seeds of the first (starting line) and second (donor plant line that comprises a desired transgene or allele) parent plants; (b) grow the seeds of the first and second parent plants into plants that bear flowers; (c) pollinate a flower from the first parent plant with pollen from the second parent plant; and (d) harvest seeds produced on the parent plant bearing the fertilized flower.

The stably transformed plant tissues and plants can be tested for providing dicamba tolerance by correct processing of DMO protein. Provision of dicamba tolerance in a crop plant can be used for designing a method for controlling weed growth in a growing environment comprising applying to the crop growing environment an amount of dicamba herbicide effective to control weed growth. The dicamba herbicide is applied over the top to the crop growing environment in an amount that does not damage the crop plant or seed transformed with a CTP-DMO construct and damages a crop plant of the same genotype lacking the CTP-DMO construct.

The preparation of herbicide compositions for use in connection with the current invention will be apparent to those of skill in the art in view of the disclosure. Such compositions, which are commercially available, will typically include, in addition to the active ingredient, components such as surfactants, solid or liquid carriers, solvents and binders. Examples of surfactants that may be used for application to plants include the alkali metal, alkaline earth metal or ammonium salts of aromatic sulfonic acids, e.g., ligno-, phenol-, naphthalene- and dibutylnaphthalenesulfonic acid, and of fatty acids of arylsulfonates, of alkyl ethers, of lauryl ethers, of fatty alcohol sulfates and of fatty alcohol glycol ether sulfates, condensates of sulfonated naphthalene and its derivatives with formaldehyde, condensates of naphthalene or of the naphthalenesulfonic acids with phenol and formaldehyde, condensates of phenol or phenolsulfonic acid with formaldehyde, condensates of phenol with formaldehyde and sodium sulfite, polyoxyethylene octylphenyl ether, ethoxylated isooctyl-, octyl- or nonylphenol, tributylphenyl polyglycol ether, alkylaryl polyether alcohols, isotridecyl alcohol, ethoxylated castor oil, ethoxylated triarylphenols, salts of phosphated triarylphenolethoxylates, lauryl alcohol polyglycol ether acetate, sorbitol esters, lignin-sulfite waste liquors or methylcellulose, or mixtures of these. Common practice in the case of surfactant use is about 0.25% to 1.0% by weight, and more commonly about 0.25% to 0.5% by weight.

Compositions for application to plants may be solid or liquid. Where solid compositions are used, it may be desired to include one or more carrier materials with the active compound. Examples of carriers include mineral earths such as silicas, silica gels, silicates, talc, kaolin, attaclay, limestone, chalk, loess, clay, dolomite, diatomaceous earth, calcium sulfate, magnesium sulfate, magnesium oxide, ground synthetic materials, fertilizers such as ammonium sulfate, ammonium phosphate, ammonium nitrate, thiourea and urea, products of vegetable origin such as cereal meals, tree bark meal, wood meal and nutshell meal, cellulose powders, attapulgites, montmorillonites, mica, vermiculites, synthetic silicas and synthetic calcium silicates, or mixtures of these.

For liquid solutions, water-soluble compounds or salts may be included, such as sodium sulfate, potassium sulfate, sodium chloride, potassium chloride, sodium acetate, ammonium hydrogen sulfate, ammonium chloride, ammonium acetate, ammonium formate, ammonium oxalate, ammonium carbonate, ammonium hydrogen carbonate, ammonium thiosulfate, ammonium hydrogen diphosphate, ammonium dihydrogen monophosphate, ammonium sodium hydrogen phosphate, ammonium thiocyanate, ammonium sulfamate or ammonium carbamate.

Other exemplary components in herbicidal compositions include binders such as polyvinylpyrrolidone, polyvinyl alcohol, partially hydrolyzed polyvinyl acetate, carboxymethylcellulose, starch, vinylpyrrolidone/vinyl acetate copolymers and polyvinyl acetate, or mixtures of these; lubricants such as magnesium stearate, sodium stearate, talc or polyethylene glycol, or mixtures of these; antifoams such as silicone emulsions, long-chain alcohols, phosphoric esters, acetylene diols, fatty acids or organofluorine compounds, and chelating agents such as: salts of ethylenediaminetetraacetic acid (EDTA), salts of trinitrilotriacetic acid or salts of polyphosphoric acids, or mixtures of these.

Dicamba may be used from about 2.5 g/ha to about 10,080 g/ha, including about 2.5 g/ha to about 5,040 g/ha, about 5 g/ha to about 2,020 g/ha, about 10 g/a to about 820 g/h and about 50 g/ha to about 1,000 g/ha, about 100 g/ha to about 800 g/ha and about 250 g/ha to about 800 g/ha.

The CTP-DMO constructs can be linked to one or more polynucleotide molecules containing genetic elements for a screenable/scorable/selectable marker and/or for a gene conferring another desired trait. Commonly used genes for screening presumptively transformed cells include β-glucuronidase (GUS), β-galactosidase, luciferase, and chloramphenicol acetyltransferase (Jefferson, 1987; Teeri et al., 1989; Koncz et al., 1987; De Block et al., 1984), green fluorescent protein (GFP) (Chalfie et al., 1994; Haseloff and Amos, 1995; and PCT application WO 97/41228). Non-limiting examples of selectable marker genes are described in, e.g., Miki and McHugh, 2004.

The nucleotide molecule conferring another desired trait may include, but is not limited to, a gene that provides a desirable characteristic associated with plant morphology, physiology, growth and development, yield, nutritional enhancement, disease or pest resistance, or environmental or chemical tolerance and may include genetic elements comprising herbicide resistance (U.S. Pat. Nos. 6,803,501; 6,448, 476; 6,248,876; 6,225,114; 6,107,549; 5,866,775; 5,804,425; 5,633,435; 5,463,175), increased yield (U.S. Pat. Nos. RE38, 446; 6,716,474; 6,663,906; 6,476,295; 6,441,277; 6,423,828; 6,399,330; 6,372,211; 6,235,971; 6,222,098; 5,716,837), insect control (U.S. Pat. Nos. 6,809,078; 6,713,063; 6,686, 452; 6,657,046; 6,645,497; 6,642,030; 6,639,054; 6,620,988; 6,593,293; 6,555,655; 6,538,109; 6,537,756; 6,521,442; 6,501,009; 6,468,523; 6,326,351; 6,313,378; 6,284,949; 6,281,016; 6,248,536; 6,242,241; 6,221,649; 6,177,615; 6,156,573; 6,153,814; 6,110,464; 6,093,695; 6,063,756; 6,063,597; 6,023,013; 5,959,091; 5,942,664; 5,942,658; 5,880,275; 5,763,245; 5,763,241), fungal disease resistance (U.S. Pat. Nos. 6,653,280; 6,573,361; 6,506,962; 6,316,407; 6,215,048; 5,516,671; 5,773,696; 6,121,436; 6,316,407; 6,506,962), virus resistance (U.S. Pat. Nos. 6,617,496; 6,608, 241; 6,015,940; 6,013,864; 5,850,023; 5,304,730), nematode resistance (U.S. Pat. No. 6,228,992), bacterial disease resistance (U.S. Pat. No. 5,516,671), plant growth and development (U.S. Pat. Nos. 6,723,897; 6,518,488), starch production (U.S. Pat. Nos. 6,538,181; 6,538,179; 6,538,178; 5,750, 876; 6,476,295), modified oils production (U.S. Pat. Nos. 6,444,876; 6,426,447; 6,380,462), high oil production (U.S. Pat. Nos. 6,495,739; 5,608,149; 6,483,008; 6,476,295), modified fatty acid content (U.S. Pat. Nos. 6,828,475; 6,822, 141; 6,770,465; 6,706,950; 6,660,849; 6,596,538; 6,589,767; 6,537,750; 6,489,461; 6,459,018), high protein production (U.S. Pat. No. 6,380,466), fruit ripening (U.S. Pat. No. 5,512, 466), enhanced animal and human nutrition (U.S. Pat. Nos. 6,723,837; 6,653,530; 6,5412,59; 5,985,605; 6,171,640), biopolymers (U.S. Pat. Nos. RE37,543; 6,228,623; 5,958,745 and U.S. Patent Publication No. US20030028917), environmental stress resistance (U.S. Pat. No. 6,072,103), pharmaceutical peptides and secretable peptides (U.S. Pat. Nos. 6,812,379; 6,774,283; 6,140,075; 6,080,560), improved processing traits (U.S. Pat. No. 6,476,295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689,041), fiber production (U.S. Pat. Nos. 6,576,818; 6,271,443; 5,981,834; 5,869,720) and biofuel production (U.S. Pat. No. 5,998,700). Any of these or other genetic elements, methods, and transgenes may be used with the invention as will be appreciated by those of skill in the art in view of the instant disclosure.

Alternatively, the one or more polynucleotide molecule linked to CTP-DMO construct can effect the above mentioned plant characteristic or phenotype by encoding a RNA molecule that causes the targeted inhibition of expression of an endogenous gene, for example, via antisense, inhibitory RNA (RNAi), or cosuppression-mediated mechanisms. The RNA could also be a catalytic RNA molecule (i.e., a ribozyme) engineered to cleave a desired endogenous mRNA product. Thus, any polynucleotide molecule that encodes a transcribed RNA molecule that affects a phenotype or morphology change of interest may be useful for the practice of the present invention.

The present invention also discloses a method for producing food, feed, or an industrial product comprising a plant containing a CTP-DMO construct or a part of such a plant and preparing the food, feed, fiber, or industrial product from the plant or part thereof, wherein the food or feed is grain, meal, oil, starch, flour, or protein and the industrial product is biofuel, fiber, industrial chemicals, a pharmaceutical, or nutraceutical.

Another aspect of the invention relates to a method for improving the standability of a monocot plant comprising: a) obtaining and growing a plant produced by crossing a parent plant with itself or with a second plant, wherein the parent plant and/or the second plant comprises the DNA construct and the dicamba tolerant plant inherits the DNA construct from said parent plant and/or the second plant; and b) treating the plant with dicamba. Parameters relating to standability may be measured, for instance including brace root number, shape, length or structure; percent lodging; and yield. In certain embodiments, the plant is a corn plant.

EXAMPLES

The following examples are included to illustrate embodiments of the invention. It should be appreciated by those of skill in the art that the techniques disclosed in the examples that follow represent techniques discovered by the inventor to function well in the practice of the invention. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Preparation of CTP-DMO Constructs for Transformation

DNA constructs as shown in Table 2 were prepared according to standard methods (e.g. Sambrook et al., 1989), comprising a CTP operably linked with a DMO gene, or a variant thereof, between a plant promoter and a polyadenylation signal sequence. These constructs were tested in either a corn protoplast system or in stably transformed *Arabidopsis* or soybean plants as described below.

TABLE 2

Processing of DMO and DMO variants by different CTPs.

| pMON | Promoter | CTP | PRT SEQ ID | DNA SEQ ID | DMO version | 3'UTR | Test System | # of Bands | Band Size (band 1/band 2) | % total expression (band 1/band 2) |
|---|---|---|---|---|---|---|---|---|---|---|
| 84254 | PCISV | PsRbcS CTP with coding region | 1 | 12 | DMOc-native(A) | RbcS 2-E9 | Soybean Leaf | 2 | 41 kDa/38 kDa | 10/90 |
| 58498 | PCISV | PsRbcS CTP with coding region | 1 | 12 | DMOc-native(A) | RbcS 2-E9 | Soybean Leaf | 2 | 41 kDa/38 kDa | 50/50 |
| 73749 | PCISV | PsRbcS CTP with coding region | 1 | 12 | DMOc-dc(A) | E6 | *Arabidopsis* Leaf | 2 | 41 kDa/38 kDa | 50/50 |
| 73725 | PCISV | PsRbcS CTP without coding region | 2 | 13 | DMOw-dc(A) | Nos | *Arabidopsis* Leaf | 1 | 38 kDa | 100 |
| 73728 | PCISV | PsRbcS CTP without coding region | 2 | 13 | DMOw-dc(L) | Nos | *Arabidopsis* Leaf | 1 | 38 kDa | 100 |
| 73729 | PCISV | AtRbcS CTP (CTP1) | 3 | 14 | DMOw-dc(A) | Nos | Corn Protoplasts | 1 | >41 kDa | 100 |
| 73708 | PCISV | AtRbcS CTP (CTP1) | 3 | 14 | DMOw-mc(L) | Hsp17 | Corn Protoplasts | 1 | >41 kDa | 100 |
| 73698 | FMV 35S | AtRbcS CTP (CTP1) | 3 | 14 | DMOc-dc(L) | RbcS 2-E9 | *Arabidopsis* Leaf | 1 | >41 kDa | 100 |
| 73731 | CaMV 35S-enh | AtShkG CTP (CTP2) | 4 | 15 | DMOw-mc(L) | Hsp17 | Corn Protoplasts | 1 | ~38 kDa | 100 |
| 73740 | PCISV | AtShkG CTP (CTP2) | 4 | 15 | DMOc-native(L) | Nos | Corn Protoplasts | 1 | ~38 kDa | 100 |
| 73713 | PCISV | AtShkG CTP (CTP2synthetic) | 5 | 16 | DMOw-mc(L) | Hsp17 | Corn Protoplasts | 1 | ~38 kDa | 100 |
| 73742 | PCISV | AtShkG CTP (CTP2synthetic) | 5 | 16 | DMOc-native(L) | Hsp17 | Corn Protoplasts | 1 | ~38 kDa | 100 |
| 73724 | PCISV | AtShkG CTP (CTP2synthetic) | 5 | 16 | DMOw-dc(A) | Nos | *Arabidopsis* Leaf | 1 | ~38 kDa | 100 |
| 73727 | PCISV | AtShkG CTP (CTP2synthetic) | 5 | 16 | DMOw-dc(L) | Nos | *Arabidopsis* Leaf | 2 | >38 kDa/ ~38 kDa | 50/50 |
| 73736 | CaMV 35S-enh | PhShkG CTP (CTP4synthetic) | 6 | 17 | DMOw-mc(L) | Hsp17 | Corn Protoplasts | 1 | ~38 kDa | 100 |
| 73747 | PCISV | PhShkG CTP (CTP4synthetic) | 6 | 17 | DMOw-mc(L) | Hsp17 | Corn Protoplasts | 1 | ~38 kDa | 100 |
| 73714 | PCISV | TaWaxy CTPsynthetic | 7 | 18 | DMOw-mc(L) | Hsp17 | Corn Protoplasts | 0 | — | — |
| 73716 | PCISV | TaWaxy CTPsynthetic | 7 | 18 | DMOw-mc(L) | Hsp17 | Corn Protoplasts | 0 | — | — |

TABLE 2-continued

Processing of DMO and DMO variants by different CTPs.

| pMON | Promoter | CTP | PRT SEQ ID | DNA SEQ ID | DMO version | 3'UTR | Test System | # of Bands | Band Size (band 1/band 2) | % total expression (band 1/band 2) |
|---|---|---|---|---|---|---|---|---|---|---|
| 73733 | CaMV 35S-enh | OsWaxy CTP | 8 | 19 | DMOw-mc(L) | Hsp17 | Corn Protoplasts | 1 | <38 kDa | 100 |
| 73734 | CaMV 35S-enh | NtRbcS CTP | 9 | 20 | DMOw-mc(L) | Hsp17 | Corn Protoplasts | 2 | >41 kDa/38 kDa | 75/25 |
| 73732 | CaMV 35S-enh | ZmAS CTP | 10 | 21 | DMOw-mc(L) | Hsp17 | Corn Protoplasts | 1 | >38 kDa | 100 |
| 73735 | CaMV 35S-enh | RgAS CTP | 11 | 22 | DMOw-mc(L) | Hsp17 | Corn Protoplasts | 1 | >38 kDa | 100 |

Example 2

Analysis of CTP-DMO Constructs in Corn Protoplasts

Corn (maize) leaf mesophyll protoplasts were prepared from 12 days old etiolated seedlings (from a LH200×LH5 cross). The middle parts of the second leaves (about 6 cm in length) were cut to 0.5-mm strips with a razor blade and digested in a flask in an enzyme solution containing 2% (w/v) cellulase RS, 0.3% (w/v) macerozyme R10 (both from Karlan Research Products Corp, Santa Rosa, Calif.), 0.6 M mannitol, 10 mM MES (pH 5.7) and 1 mM $CaCl_2$, for no more than 2 hr at 23° C. after 30 minutes of vacuum infiltration. Protoplasts from infiltrated and digested leaf tissue were released by shaking the flask by hand for 5 min and separated by filtering through a 60-μm nylon mesh. The protoplasts were collected by centrifugation at 150 g for 2 min, washed in cold 0.6 M mannitol solution once, centrifuged, and resuspended at a $2\times10^6$/mL in cold 0.6 M mannitol. The protoplasts were then transformed with 12.5 μg DNA using polyethylene glycol (PEG) and incubated at room temperature for 16 to 20 hr.

The protoplasts were stored at −80° C. until analysis by western blot. The protoplasts were thawed on ice and 1-3 volumes of 2× Laemmli sample buffer/dye (BioRad) with 5.0% β-ME was added to the protoplasts. Aliquots of the protoplast protein samples were then heated to about 100° C. for 5 minutes and loaded onto a pre-cast Tris-HCL 10% polyacrylamide gel. Electrophoresis was performed at a constant current of about 80-100 Amps for about 35 minutes. Protein from the gel was electro-transferred to a 0.2 micron nitrocellulose membrane for 1-3 hours at a constant voltage of 100 V. The membrane was blocked for one hour at room temperature or overnight at 4° C. with 5% (w/v) dry milk in TBST. The membrane was probed with a 1:200 dilution of goat anti-DMO antibody in TBST for one hour. Excess antibody was removed using three 5 min washes with TBS. The membrane was probed with peroxidase-conjugated rabbit anti-goat IgG (Sigma, St. Louis, Mo.) at a dilution of 1:7,500 in 0.5% (w/v) dry milk in TBST for one hour. Excess peroxidase-conjugate was removed using three 5 min washes with TBST. All procedures, including blocking, and all other incubations were performed at room temperature, except where noted. Immunoreactive bands were visualized using the ECL detection system (Amersham Biosciences, Piscataway, N.J.) and exposed to Kodak BioMax™ MS film. The presence of immunoreactive bands of the appropriate size indicates proper processing and localization of DMO (Table 1). Thus, for instance, use of CTP4 operably linked to DMO and transformed into corn protoplasts results in a 38 kDa immunoreactive band following western blot analysis.

Example 3

Testing of Various CTP-DMO Constructs in *Arabidopsis*

*Arabidopsis thaliana* ecotype Columbia plants were transformed according to the method developed by Clough and Bent (1998). Seeds obtained through this method were plated on a plant culture selection medium containing dicamba at various concentrations from 0.5, 1.0, to 2.0 or 4.0 mg/liter. The plates were incubated for 48 hours at 4° C. and then transferred to a Percival incubator set at 23.5° C. with a photoperiod of 16 hours. Seeds that were transformed with CTP-DMO constructs grew into plants on dicamba containing medium and developed primary and secondary leaves, while the untransformed seed and negative segregants either died or did not develop primary and secondary leaves. The transgenic plants that tested positive for the 3' UTR by Invader® PCR assay were used further for analysis.

Three to five leaf punches from the transgenic *Arabidopsis* plants were used for western blot analysis. Protein extraction was performed with 500-1000 μl PSBT and 4 glass beads in a Harbil paint shaker for 3 minutes. Samples were spun at 3000 rpm for 3 minutes at 4° C. An equal volume of 2× Laemmli sample buffer/dye (cat. No. 161-0737 BioRad) with 5.0% β-ME was added to aliquots of the supernatant. Remaining steps of the western blot analysis were the same as in Example 2. The presence of immunoreactive bands of the appropriate size indicates proper processing and localization of DMO (Table 2). For instance, as shown in Table 2, in a comparison of bands seen following transformation of *Arabidopsis* with pMON73749 or pMON73725, use of RbcSnoc-CTP, lacking the 27 aa coding sequence derived from pea Rubisco enzyme resulted in properly processed DMO localized to the chloroplast, while use of the RbcS CTP including the 27 aa coding sequence resulted in two immunoreactive bands.

Example 4

Testing of CTP-DMO Constructs in Soybean

Transgenic soybean (e.g. cvs. Thorne, NE3001 and A3525) plants were obtained by *Agrobacterium*-mediated transformation of soybean using standard procedures (e.g. Zhang et al., 1999; U.S. Pat. No. 7,002,058). Three to five leaf punches from the transgenic soybean plants were used for western blot analysis. Protein extraction was performed with 500-1000 μl PSBT and 4 glass beads in a Harbil paint shaker for 3 min. Samples were spun at 3000 rpm for 3 minutes at 4° C. An equal volume of 2× Laemmli sample buffer/dye (BioRad) w/5.0% β-ME was added to aliquots of the supernatant. The remaining steps of the western blot analysis were the same as in Example 2. The presence of immunoreactive bands of the appropriate size indicates proper processing and localization of DMO (Table 2).

Soybean plants that were transformed with a construct coding for a DMO linked to a pea Rubisco transit peptide attached to an additional 24 amino acids of the Rubisco coding region, and 3 amino acids due to introduction of restriction enzyme recognition sites, showed an injury rate of 17-20% when treated with 0.5 lb of dicamba at pre emergence stage followed by 2 lb of dicamba at post emergence (V6) stage. This compares with soybean plants that were transformed with a construct coding for a DMO linked to a pea Rubisco transit peptide only, that showed an injury rate of about 12%. These results indicate that use of a transit peptide without additional amino acids results in production of a single DMO activity (rather than multiple partially or differently processed polypeptides) and higher tolerance to dicamba. Production of a single form of the enzyme will also lead to ease of product characterization and reduced cost of registration.

Example 5

Efficient Production of DMO and Higher Tolerance to Dicamba Requires a CTP

*Arabidopsis thaliana* ecotype Columbia plants were transformed with several constructs (FIG. 1) as described in Example 3. Transformed seeds were selected on a plant tissue culture medium containing dicamba at various concentrations from 0.5, 1.0, to 2.0 mg/liter. Seeds that were transformed with CTP-DMO constructs grew into plants on dicamba containing medium and developed primary and secondary leaves, while the untransformed seed and negative segregants either died or did not develop primary and secondary leaves. The transgenic plants that grew and tested positive for the DMO gene were used further for analysis.

As shown in FIG. 1, plants that were transformed with constructs without a CTP exhibited little or no tolerance to dicamba. Soybean plants transformed with a DNA construct coding for a DMO without linking it to a CTP showed no pre emergence tolerance whereas plants transformed with constructs where the DMO was linked to the CTP showed both pre and post emergence tolerance to dicamba when treated with 0.5 lb/a of dicamba at pre emergence stage followed by 2 lb/a of dicamba at post emergence (V6) stage.

Example 6

Production of Dicamba Tolerant Transgenic Corn Plants

To test the use of a DMO gene in providing dicamba tolerance to monocots, transgenic corn plants were produced that comprise a DMO gene (e.g. SEQ ID NOS: 29, 33, 35, 37, 39) with or without a transit peptide (e.g. TaWaxy, CTP1, CTP2synthetic, CTP4) under the control of plant gene expression elements such as a promoter (e.g. PClSV, e35S, OsAct1, OsTPI, OsAct15), and an intron (e.g. OsAct1, OsAct15, OsTPI, ZmHSP70). This expression element contains first intron and flanking UTR exon sequences from the rice actin 1 gene and includes 12 nt of exon 1 at the 5' end and 7 nt of exon 2 at the 3' end), and a 3'UTR (e.g. TaHsp17).

Transgenic corn plants were produced essentially by the method described in U.S. patent application 20040244075. Transgenic corn events having single copy were evaluated for dicamba tolerance at a single location replicated trial. Six events from each of the six constructs were used. The experimental design was as follows: rows/entry: 1; treatment: 0.5 lb/a of dicamba at V3 stage followed by 1 lb/a of dicamba at V8 stage (Clarity®, BASF, Raleigh, N.C.); replications: 2; row spacing: 30 inches; plot length: minimum 20 feet; plant density: about 30 plants/17.5 ft.; alleys: 2.5 feet. The entire plot was fertilized uniformly to obtain an agronomically acceptable crop. A soil insecticide such as Force® 3G (Syngenta Crop Protection, Greensboro, N.C., USA) at 5 oz. per 1000 ft. of row for control of corn rootworm was applied at planting time. If black cutworm infestation was observed, POUNCE® 3.2EC at 4 to 8 oz. per acre rate (FMC Corporation, Philadelphia, Pa.) was used. In addition, an insecticide spray program was used to control all above ground lepidopteran pests including European corn borer, corn earworm, and fall armyworm. POUNCE® 3.2EC at 4 to 8 oz. per acre was applied every 3 weeks to control lepidopteran pests; about 4 applications were made. The plot was kept weed free with a pre-emergence application of a herbicide such as Harness® Xtra 5.6L (Monsanto, St. Louis, Mo.) and Degree Xtra® (Monsanto, St. Louis, Mo.). If weed escapes were observed in the untreated check, they were controlled by hand weeding or a post-emergence application of PERMIT (Monsanto, St. Louis, Mo.) or BUCTRIL® (Bayer, Research Triangle Park, N.C.) over the entire trial.

Corn inbred lines transformed with DNA constructs comprising a DMO transgene were tested for dicamba tolerance by measuring brace root injury when treated with 0.5 lb/a of dicamba at V3 stage followed by 1 lb/a of dicamba at V8 stage. Brace root injury was evaluated visually by counting the number of plants in a row showing an "atypical" morphology of having the brace roots fused as compared to a typical morphology of "finger-like" structure. As shown in Table 3, corn plants transformed with DNA constructs coding for a DMO without linking it to a CTP (pMON73699, pMON73704) showed higher level of brace root injury, i.e. lower level of protection upon dicamba treatment. The constructs coding for a DMO linked to a CTP (pMON73716, pMON73700, pMON73715, pMON73703) showed lower level of brace root injury, i.e. higher level of protection upon dicamba treatment.

TABLE 3

Percentage brace root injury exhibited by transgenic corn plants transformed with DNA constructs carrying DMO when tested for dicamba tolerance.

| Inbreds/Constructs | Details | Brace root injury |
| --- | --- | --- |
| 01CSI6 | Susceptible inbred to dicamba | 95.4 |
| LH244 | Resistant inbred to dicamba | 93.8 |
| pMON73699 | PC1SV/I-OsAct1/DMO-Wmc/TaHsp17 | 93.2 |
| pMON73704 | e35S/I-OsAct1/DMO-Wmc/TaHsp17 | 91.3 |

TABLE 3-continued

Percentage brace root injury exhibited by transgenic corn plants transformed with DNA constructs carrying DMO when tested for dicamba tolerance.

| Inbreds/Constructs | Details | Brace root injury |
|---|---|---|
| pMON73716 | PC1SV/I-OsAct1/TaWaxy/DMO-Wmc/TaHsp17 | 78.8 |
| pMON73700 | PC1SV/I-OsAct1/CTP1/DMO-Wmc/TaHsp17 | 74.4 |
| pMON73715 | PC1SV/I-OsAct1/CTP2syn/DMO-Wmc/TaHsp17 | 68.2 |
| pMON73703 | e35S/I-OsAct1/CTP1/DMO-Wmc/TaHsp17 | 68.8 |

From these studies in diverse plant species (also, e.g. Examples 3, 4 and 8), a chloroplast transit peptide is useful for efficient targeting of DMO and full production of DMO activity, leading to higher tolerance to dicamba. Further, expression of a CTP-DMO provides pre-emergence tolerance to dicamba in corn.

Example 7

Construction of Efficient DMO Expression Units

Several genetic elements can influence efficient expression of a gene such as a promoter, chloroplast transit peptide sequence, an intron, 5'UTR, coding region of the gene, 3'UTR. However, it is not obvious which combination will work the best. Efficient DMO expression units or constructs are required to produce improved products such as a dicamba tolerant seed and plant. Several DMO expression units were constructed by operably linking one of each various promoters, CTPs, DMO variants, and 3'UTRs to obtain efficient DMO expression units for product development. These constructs were transformed into soybean by methods known in the art (e.g. U.S. Pat. No. 6,384,301, U.S. Pat. No. 7,002,058 or Zhang et al., 1999). Transgenic seeds were obtained and tested for pre- and post-emergence tolerance to dicamba herbicide. Table 4 shows the % injury caused by dicamba (lower injury means higher tolerance) when seeds and plants were treated with 0.5 lb/acre of dicamba pre-emergent followed by 2 lb/acre of dicamba post-emergent at V6 stage. Seeds transformed with DNA constructs pMON68939 and pMON73723 that carried no CTP were unable to tolerate pre-emergent application of dicamba indicating that targeting of DMO to chloroplast is required to obtain pre-emergence tolerance to dicamba. Plants transformed with pMON68939 and pMON73723 (without CTP) that were treated with dicamba at post-V3 stage at 1 lb/a rate showed injury rate of 55% and 57% respectively similar to the wild type soybean (60%) whereas the plants transformed with pMON68938 (with CTP) showed very little injury. These results indicate that a CTP is required for obtaining both pre and post emergence tolerance to dicamba in soybean.

TABLE 4

Percentage injury exhibited by soybean plants transformed with a specific DMO expression unit and treated with dicamba pre-emergent and post-emergent.

| Expression Unit | pMON designation | % Injury |
|---|---|---|
| PC1SV/CTP2syn/DMO-Wat(A)/nos | 73724 | 9 |
| e35S/CTP1/DMO-Wat(L)/nos | 68938 | 12 |
| PC1SV/RbcSnoc/DMO-Wat(A)/nos | 73725 | 12 |
| PC1SV/RbcSnoc/DMO-Wat(L)/nos | 73728 | 12 |
| PCSV/CTP1/DMO-Wat(A)/nos | 73729 | 13 |

TABLE 4-continued

Percentage injury exhibited by soybean plants transformed with a specific DMO expression unit and treated with dicamba pre-emergent and post-emergent.

| Expression Unit | pMON designation | % Injury |
|---|---|---|
| PC1SV/CTP2syn/DMO-Wat(L)/nos | 73727 | 13 |
| ANT1/CTP1/DMO-Wat(L)/nos | 68945 | 14 |
| PC1SV/RbcSnoc/DMO-Wat(A)/nos | 73730 | 15 |
| PC1SV/RbcS-CTP/DMO-Cnat(A)/nos | 68934 | 17 |
| Act7/CTP1/DMO-Wat(L)/nos | 68942 | 17 |
| FMV.35S-EF1a/CTP1/DMO-Wat(L)/nos | 68940 | 17 |
| PC1SV/RbcS-CTP/DMO-Cnat(A)/E9 | 84254 | 20 |
| FMV/CTP1/DMO-Wat(L)/nos | 68941 | 29 |
| eIF4A10/CTP1/DMO-Wat(L)/nos | 68943 | 60 |
| e35S/CTP1/DMO-Cat(A)/nos | 68937 | 62 |
| e35S/CTP1/DMO-Cnat(L)/nos | 68946 | 73 |
| e35S/DMO-Wat(A)/nos | 68939 | 100 (Pre) |
| PC1SV/DMO-Wat(A)/nos | 73723 | 100 (Pre) |

Example 8

Production of Dicamba Tolerant Transgenic Cotton Plants

To test the use of DMO gene in providing dicamba tolerance to cotton, transgenic cotton plants were produced. Several DNA constructs carrying a DMO coding region (e.g. SEQ ID NOS: 23, 25, 27, 29, 31, 35) with a transit peptide (e.g., PsRbcS CTP, CTP1, CTP2) under the control of plant gene expression elements such as a promoter (e.g. PC1SV, FMV, or e35S), and a 3'UTR (e.g. E6; Accession # U30508) were produced and transformed into cotton (*Gossypium hirsutum*) as follows. Media used are noted in Table 5.

Seedlings of cotton cv Coker 130 were grown in vitro and hypocotyl sections were cut and inoculated with a liquid suspension of *Agrobacterium tumefaciens* carrying a DNA construct, blot dried, and co-cultured for 2 days. Inoculated hypocotyl explants were then transferred to glucose selection medium for 4 weeks, sucrose selection medium for 1 week, and to glucose selection medium for an additional 4 weeks for inducing callus. The cultures were incubated in 16/8 (light/dark) cycle and 28° C. temperature. Kanamycin resistant calli were then transferred to UMO medium and cultured in the dark for 16-24 weeks at 28-30° C. for inducing embryogenic callus. The embryogenic callus was then harvested from these calli and maintained for up to 4-16 weeks in the dark at 28-30° C. on TRP+ medium. Small embryos from the embryogenic callus were harvested and germinated on SHSU medium in 16/8 (light/dark) cycle and 28-30° C. temperature. Plantlets that appeared normal were then transferred to soil to obtain mature cotton plants. The transgenic nature of transformants was confirmed by DNA testing.

TABLE 5

Composition of various media used for cotton transformation.

| Components | Amount/L | | | | |
|---|---|---|---|---|---|
| | Glucose | Sucrose | UMO | TRP+ | SHSU |
| MS basal salts (Phytotech.) | 4.33 g | 4.33 g | 4.33 g | 4.33 g | — |
| Gamborg's B5 vitamins (Phytotech) (500X) | 2 ml | 2 ml | 2 ml | 2 ml | — |
| 2,4-D (1 mg/ml) | 0.1 ml | 0.1 ml | — | — | — |
| Stewart and Hsu majors (10X) | — | — | — | — | 100 ml |
| Stewart and Hsu minors (100X) | — | — | — | — | 10 ml |
| Steward and Hsu organic (100X) | — | — | — | — | 10 ml |
| Kinetin (0.5 mg/ml) | 1 ml | 1 ml | — | — | — |
| Chelated iron (100X) | — | — | — | — | 1.5 ml |
| Glucose | 30 g | 30 g | 30 g | 30 g | 5 g |
| Potassium nitrate | — | — | — | 1.9 g | — |
| Casein hydrolysate | — | — | — | 0.1 g | — |
| pH | 5.8 | 5.8 | 5.8 | 5.8 | 6.8 |
| Phytagel (Sigma) | 2.5 g | 2.5 g | — | — | — |
| Gelrite (Kelco) | — | — | 3.5 g | 3.5 g | 2.2 g |
| Carbenicillin (250 mg/ml) | 1.7 ml | 1.7 ml | 1.7 ml | 1.7 ml | — |
| Cefotaxime (100 mg/ml) | 1 ml | 1 ml | 1 ml | 1 ml | — |
| Benlate (50 mg/ml) | — | — | — | 1 ml | 1 ml |
| Kanamycin (50 mg/ml) | 0.8-1.0 ml | 0.8-1.0 ml | 1 ml | — | — |
| Sucrose | — | 0.1 g | — | — | — |
| Ascorbic acid | — | — | 100 mg | — | — |

Transformed cotton plants that comprise such a DNA construct, each comprising a different combination of a DMO coding region with a transit peptide, a promoter, and a 3'UTR, were treated with dicamba (Clarity®, BASF, Raleigh, N.C.) as a post-emergent treatment at V4-5 growth stage at the rate of 561 g ae/ha (0.5 lb/a) and found to be tolerant whereas untransformed cotton plants showed an injury rate of 79% to 86%. Transgenic plants showing more than 95% tolerance (equal to less than 5% injury) were selected for further studies. Transgenic plants were also tolerant to a subsequent post-emergent treatment of dicamba. For example, the plants that were treated with 0.5 lb/acre of dicamba at V3-4 stage followed by either 1 or 2 lb/acre of dicamba at V5 or later stages were still tolerant to dicamba. This examples shows that a DMO gene can provide dicamba tolerance to cotton at various stages of growth thus enabling application of dicamba at various stages to obtain effective weed control.

Example 9

Method for Improving Standability of Corn

Certain monocots such as corn produce brace roots which grow from the nodes above the soil surface and help support the plant and scavenge the upper soil layers for water and nutrients during the reproductive stages. A healthy brace root system becomes important if the plants are subjected to high winds or when the underground root system becomes weaker by root worm infection or under soil water deficit. Synthetic herbicide such as dicamba and 2,4-D are permitted for use on monocots such as corn for broad leaf weed control. For post-emergent weed control in corn, dicamba is the 5th most widely used herbicide. Although the optimal rate for broad leaf weed control is between 280 to 560 grams/hectare (g/h) or 0.25 to 0.5 lb/acre, the average use rate in corn is 168 g/h or 0.15 lb/acre as at higher rates and under certain environmental conditions such as on hot days, dicamba can injure corn. In addition, several corn hybrids such as DKC61-42, DKC64-77, DKC63-46, DKC66-21 and DKC61-44 and inbreds such as 01CSI6, 16IUL2, 70LDL5, and 90LCL6 are sensitive to dicamba applications. The sensitivity is manifested in many ways such as occurrence of onion leafing, tassel malformation, reduced plant height, or abnormal brace root formation e.g. fused or twisted root formation. The brace roots become gnarled, tending to grow together and not growing into the soil to support the plant. This may result in poor standability of a corn crop, higher susceptibility to lodging, and eventually yield loss. Several herbicide products that contain dicamba, for example Clarity®, BANVEL, MARKSMAN, DISTINCT, NORTHSTAR, and CELEBRITY PLUS, can cause these effects. Increasing tolerance of corn to dicamba will also be useful in protecting corn fields planted closer to crop species such as soybean and cotton that are tolerant to dicamba and where a higher rate of dicamba application is permitted.

The present example provides a method for improving standability of corn and other monocots by incorporating a DMO gene in corn and treating corn with dicamba. In one embodiment, the DMO gene is expressed under the control of a constitutive promoter that is also capable of expressing DMO in nodal region and/or in brace roots. In another embodiment the DMO gene is expressed under the control of a chimeric constitutive and node/brace root specific promoter. In another embodiment the DMO gene is expressed under the control of a root specific promoter such as RCc3 or a variant thereof (e.g. SEQ ID NOs:1-6 as found in US20060101541). The expression of DMO in brace roots results in no or less injury to brace roots resulting in better standability of corn, less lodging, and therefore better yield.

R1 or F1 seeds of three single copy events from corn plants transformed with various DMO constructs (outlined in Table 6) were germinated in 4.0" trays. Healthy plants were transplanted into about 10" pots. Germination and growth media comprised of Redi-Earth™ (Scotts-Sierra Horticultural Products Co., Marysville, Ohio). The pots were placed on capillary matting in 35 inch×60 inch fiberglass watering trays for sub-irrigation for the duration of the test period so as to maintain optimum soil moisture for plant growth. The pots were fertilized with Osmocote (14-14-14 slow release; Scotts-Sierra Horticultural Products Co., Marysville, Ohio) at the rate of 100 gm/cu.ft. to sustain plant growth for the duration of greenhouse trials. The plants were grown in greenhouses at 29°/21° C. day/night temperature, with relative humidity between 25%-75% to simulate warm season growing conditions of late spring. A 14 h minimum photoperiod was provided with supplemental light at about 600 μE as needed.

Dicamba applications were made with the track sprayer using a Teejet 9501E flat fan nozzle (Spraying Systems Co, Wheaton, Ill.) with air pressure set at a minimum of 24 psi (165 kpa). The spray nozzle was kept at a height of about 16 inches above the top of plant material for spraying. The spray volume was 10 gallons per acre or 93 liters per hectare. Applications were made when plants had reached V 4-5 leaf stage.

Plants of a corn inbred line transformed with DNA constructs comprising a DMO expression unit were tested for brace root injury and lodging by treating with 2 lb/acre or 4 lb/acre of dicamba at V4-5 stage and evaluating the plants for brace root injury (0%; no visible plant injury) to 100% (complete death of plant); and lodging (degree of leaning) at 24 DAT.

As shown in Table 6, corn plants transformed with the DNA constructs having a DMO expression unit showed no or little brace root injury and lodging as compared to untransformed control inbred line and plants transformed with a selectable marker expression unit only (pMON73746). This example shows that DMO containing plants provide can used to provide improved standability when treated with dicamba.

TABLE 6

Corn plants transformed with various DMO constructs show no or little injury to brace roots and lodging when treated with dicamba.

| Inbred/construct | Event | Details of construct | Dicamba Application Level | |
|---|---|---|---|---|
| | | | 2 lb/acre | 4 lb/acre |
| | | | % brace root injury and lodging at | |
| | | | 24 DAT | 24 DAT |
| control | | | 17.5 | 31.7 |
| 73746 R1 | S214540 | No DMO expression unit | 20.0 | 28.1 |
| 73746 F1 | S215886 | | 33.8 | 40.0 |
| 73703 F2 | S183001 | e35S/I-OsAct1/CTP1-DMO Wmc/TaHsp17 | 0.9 | 1.0 |
| 73744 F1 | S208388 | OsAct1/I-OsAct1/CTP2syn-DMOWmc/TaHsp17 | 0.0 | 0.2 |
| 73744 F1 | S208373 | | 0.0 | 0.4 |
| 73744 F1 | S208382 | | 0.0 | 0.0 |
| 73747 R1 | S207612 | PC1SV/I-OsAct1/CTP4-DMOWmc/TaHsp17 | 0.6 | 1.8 |
| 73747 R1 | S207608 | | 0.8 | 1.0 |
| 73747 R1 | S208367 | | 0.0 | 0.0 |
| 73743 R1 | S208476 | PCSV/I-OsAct1/CTP2syn/DMO-Cmc/TaHsp17 | 3.9 | 19.6 |
| 73743 R1 | S208469 | | 1.3 | 22.9 |
| 73743 R1 | S208071 | | 2.7 | 13.5 |
| 73742 R1 | S213404 | PC1SV/I-OsAct1/CTP2syn-DMO-Cnat/TaHsp17 | 0.0 | 0.0 |
| 73742 R1 | S213395 | | 0.2 | 0.4 |
| 73742 R1 | S212111 | | 0.4 | 0.5 |

REFERENCES

The references listed below are incorporated herein by reference to the extent that they supplement, explain, provide a background for, or teach methodology, techniques, and/or compositions employed herein.

U.S. Pat. No. 4,554,101; U.S. Pat. No. 5,015,580; U.S. Pat. No. 5,846,797; U.S. Pat. No. 5,004,863; U.S. Pat. No. 5,017,692; U.S. Pat. No. 5,159,135; U.S. Pat. No. 5,229,114; U.S. Pat. No. 5,304,730; U.S. Pat. No. 5,322,938; U.S. Pat. No. 5,352,605; U.S. Pat. No. 5,359,142; U.S. Pat. No. 5,362,865; U.S. Pat. No. 5,378,619; U.S. Pat. No. 5,384,253; U.S. Pat. No. 5,424,412; U.S. Pat. No. 5,463,175; U.S. Pat. No. 5,508,184; U.S. Pat. No. 5,512,466; U.S. Pat. No. 5,516,671; U.S. Pat. No. 5,530,196; U.S. Pat. No. 5,538,880; U.S. Pat. No. 5,543,576; U.S. Pat. No. 5,550,318; U.S. Pat. No. 5,552,299; U.S. Pat. No. 5,641,876; U.S. Pat. No. 5,567,600; U.S. Pat. No. 5,567,862; U.S. Pat. No. 5,591,616; U.S. Pat. No. 5,608,149; U.S. Pat. No. 5,633,435; U.S. Pat. No. 5,635,055; U.S. Pat. No. 5,641,876; U.S. Pat. No. 5,659,122; U.S. Pat. No. 5,689,041; U.S. Pat. No. 5,689,052; U.S. Pat. No. 5,716,837; U.S. Pat. No. 5,728,925; U.S. Pat. No. 5,750,871; U.S. Pat. No. 5,750,876; U.S. Pat. No. 5,763,241; U.S. Pat. No. 5,763,245; U.S. Pat. No. 5,773,696; U.S. Pat. No. 5,804,425; U.S. Pat. No. 5,824,877; U.S. Pat. No. 5,837,848; U.S. Pat. No. 5,850,019; U.S. Pat. No. 5,850,023; U.S. Pat. No. 5,859,347; U.S. Pat. No. 5,866,775; U.S. Pat. No. 5,869,720; U.S. Pat. No. 5,942,664; U.S. Pat. No. 5,958,745; U.S. Pat. No. 5,959,091; U.S. Pat. No. 5,981,834; U.S. Pat. No. 5,981,840; U.S. Pat. No. 5,985,605; U.S. Pat. No. 5,998,700; U.S. Pat. No. 5,942,658; U.S. Pat. No. 5,880,275; U.S. Pat. No. 6,5412,59; U.S. Pat. No. 6,011,199; U.S. Pat. No. 6,013,864; U.S. Pat. No. 6,015,940; U.S. Pat. No. 6,023,013; U.S. Pat. No. 6,051,753; U.S. Pat. No. 6,063,597; U.S. Pat. No. 6,063,756; U.S. Pat. No. 6,072,103; U.S. Pat. No. 6,080,560; U.S. Pat. No. 6,093,695; U.S. Pat. No. 6,107,549; U.S. Pat. No. 6,110,464; U.S. Pat. No. 6,121,436; U.S. Pat. No. 6,140,075; U.S. Pat. No. 6,140,078; U.S. Pat. No. 6,153,814; U.S. Pat. No. 6,156,573; U.S. Pat. No. 6,160,208; U.S. Pat. No. 6,166,292; U.S. Pat. No. 6,171,640; U.S. Pat. No. 6,175,060; U.S. Pat. No. 6,177,611; U.S. Pat. No. 6,177,615; U.S. Pat. No. 6,215,048; U.S. Pat. No. 6,221,649; U.S. Pat. No. 6,222,098; U.S. Pat. No. 6,225,114; U.S. Pat. No. 6,228,623; U.S. Pat. No. 6,228,992; U.S. Pat. No. 6,232,526; U.S. Pat. No. 6,235,971; U.S. Pat. No. 6,242,241; U.S. Pat. No. 6,248,536; U.S. Pat. No. 6,248,876; U.S. Pat. No. 6,252,138; U.S. Pat. No. 6,271,443; U.S. Pat. No. 6,281,016; U.S. Pat. No. 6,284,949; U.S. Pat. No. 6,294,714; U.S. Pat. No. 6,313,378; U.S. Pat. No. 6,316,407; U.S. Pat. No. 6,326,351; U.S. Pat. No. 6,372,211; U.S. Pat. No. 6,380,462; U.S. Pat. No. 6,380,

466; U.S. Pat. No. 6,384,301; U.S. Pat. No. 6,388,170; U.S. Pat. No. 6,399,330; U.S. Pat. No. 6,399,861; U.S. Pat. No. 6,403,865; U.S. Pat. No. 6,423,828; U.S. Pat. No. 6,426,446; U.S. Pat. No. 6,426,447; U.S. Pat. No. 6,429,357; U.S. Pat. No. 6,429,362; U.S. Pat. No. 6,433,252; U.S. Pat. No. 6,437,217; U.S. Pat. No. 6,441,277; U.S. Pat. No. 6,444,876; U.S. Pat. No. 6,448,476; U.S. Pat. No. 6,459,018; U.S. Pat. No. 6,468,523; U.S. Pat. No. 6,476,295; U.S. Pat. No. 6,476,295; U.S. Pat. No. 6,483,008; U.S. Pat. No. 6,489,461; U.S. Pat. No. 6,495,739; U.S. Pat. No. 6,501,009; U.S. Pat. No. 6,506,962; U.S. Pat. No. 6,506,962; U.S. Pat. No. 6,518,488; U.S. Pat. No. 6,521,442; U.S. Pat. No. 6,531,648; U.S. Pat. No. 6,537,750; U.S. Pat. No. 6,537,756; U.S. Pat. No. 6,538,109; U.S. Pat. No. 6,538,178; U.S. Pat. No. 6,538,179; U.S. Pat. No. 6,538,181; U.S. Pat. No. 6,555,655; U.S. Pat. No. 6,573,361; U.S. Pat. No. 6,576,818; U.S. Pat. No. 6,589,767; U.S. Pat. No. 6,593,293; U.S. Pat. No. 6,596,538; U.S. Pat. No. 6,608,241; U.S. Pat. No. 6,617,496; U.S. Pat. No. 6,620,988; U.S. Pat. No. 6,624,344; U.S. Pat. No. 6,635,806; U.S. Pat. No. 6,639,054; U.S. Pat. No. 6,642,030; U.S. Pat. No. 6,645,497; U.S. Pat. No. 6,653,280; U.S. Pat. No. 6,653,530; U.S. Pat. No. 6,657,046; U.S. Pat. No. 6,660,849; U.S. Pat. No. 6,663,906; U.S. Pat. No. 6,686,452; U.S. Pat. No. 6,706,950; U.S. Pat. No. 6,713,063; U.S. Pat. No. 6,716,474; U.S. Pat. No. 6,723,837; U.S. Pat. No. 6,723,897; U.S. Pat. No. 6,770,465; U.S. Pat. No. 6,774,283; U.S. Pat. No. 6,803,501; U.S. Pat. No. 6,809,078; U.S. Pat. No. 6,812,379; U.S. Pat. No. 6,822,141; U.S. Pat. No. 6,828,475; U.S. Pat. No. 7,022,896; U.S. Pat. No. 7,002,058; U.S. Pat. No. 7,132,528; U.S. Pat. No. 7,151,204; U.S. Pat. RE38,446; U.S. Pat. RE37,543

U.S. Patent Publn. No. 20030028917; U.S. Patent Publn. 20030135879; U.S. Patent Publication 20030115626; US Patent Publn. 20040244075; U.S. Patent Publn. No. 20050022261; U.S. Patent Publn. No. 20060101541; U.S. Patent Publn. No. 20060162010; U.S. Patent Publn. No. 20060236420.

U.S. Prov. Appl. Ser. No. 60/811,152; U.S. Prov. Appl. Ser. No. 60/884,854

Akashi et al., *FEBS Lett.* 431:39-44, 1998.
Becker et al., *Plant Mol. Biol.* 20:49, 1992.
Bevan et al., *Nature,* 304:184-187, 1983.
Bohlmann et al., *Plant J.,* 7 (3): 491-501, 1995.
Carrington and Freed, *J. of Virology* 64:1590-1597, 1990.
Chalfie et al., *Science,* 263(5148):802-805, 1994.
Chandler et al., *Plant Cell,* 1:1175-1183, 1989.
Chu et al. *Scientia Sinica* 18:659, 1975.
Clark et al., *Plant Mol. Biol.,* 16 (6): 1099-1101, 1991.
Clough and Bent, *Plant J.,* 16:735-743, 1998.
Cork and Khalil, *Adv. Appl. Microbiol.,* 40:289-321, 1995.
Cork and Krueger, *Adv. Appl. Microbiol.,* 36:1-66, 1991.
Coruzzi et al., *EMBO J.,* 3:1671-1679, 1984.
Creissen et al., *Plant J.,* 2(1):129-131, 1992.
Creissen et al., *Plant J.* 8:167-175, 1995.
De Block et al., *EMBO J.,* 3(8):1681-1689, 1984.
Depicker et al., *J. Mol. Appl. Genet.* 1:561-573, 1982.
Ebert et al., *Proc. Natl. Acad. Sci. USA,* 84:5745-5749, 1987.
European Appln. 646643
European Appln. 553494
Fraley et al., *Proc. Natl. Acad. Sci. USA,* 80:4803-4807, 1983.
Gardiner et al., *Plant Physiol.,* 134: 1317-1326, 2004.
Gasser et al., *J. Biol. Chem.,* 263: 4280-4287, 1988.
Haseloff and Amos, *Trends Genet.,* 11(8):328-329, 1995.
Herman et al., *J. Biol. Chem.,* 280(26):24759-24767, 2005.
Ingelbrecht et al., *Plant Cell,* 1:671-680, 1989.
Jefferson, *Plant Mol. Biol. Rep.,* 5:387-405, 1987.
Klee et al., *Mol. Gen. Genet.,* 210:437-442, 1987.
Koncz et al., *Proc. Natl. Acad. Sci. USA,* 84(1):131-135, 1987.
Kyte and Doolittle, *J. Mol. Biol.,* 157(1):105-132, 1982.
Lawton et al., *Plant Mol. Biol.* 9:315-324, 1987.
Mazur, et al., *Nucleic Acids Res.,* 13(7):2373-2386, 1985.
Miki and McHugh, *J. Biotechnol.* 107:193-232, 2004.
Miki et al., In: *Methods in Plant Molecular Biology and Biotechnology,* Glick and Thompson (Eds.), CRC Press, 67-88, 1993.
Moberg et al., *Plant J.* 36:616-628, 2003.
Murashige and Skoog, *Physiol Plant* 15:473-497, 1962.
Odell et al., *Nature,* 313:810-812, 1985.
Okagaki, *Plant Mol. Biol.,* 19: 513-516, 1992.
PCT Appln. WO 9506722.
PCT Appln. WO 97/11086
PCT Appln. WO 97/31115
PCT Appln. WO 97/41228
Rudhe et al., *J. Molec. Biol.* 324:577-585, 2002.
Sambrook et al., In: *Molecular cloning: a laboratory manual,* $2^{nd}$ Ed., Cold Spring Harbor Laboratory Press, Cold Spring Harbor, N.Y., 1989.
Silva Filho et al., *Plant Molecular Biology* 30:769-780, 1996,
Teeri et al., *EMBO J.,* 8(2):343-350, 1989.
Turner and Foster, *Molecular Biotech.,* 3:225, 1995.
Walker et al., *Proc. Natl. Acad. Sci. USA,* 84:6624, 1987.
Yang and Russell, *Proc. Natl. Acad. Sci. USA,* 87:4144-4148, 1990.
Zhang et al., *Plant Cell Tissue Organ Cult.* 56:37-46, 1999.

The invention claimed is:

1. A recombinant DNA molecule comprising a DNA sequence encoding a chloroplast transit peptide operably linked to a DNA sequence encoding dicamba monooxygenase, wherein the DNA sequence encoding the chloroplast transit peptide encodes SEQ ID NO:1.

2. The recombinant DNA molecule of claim 1, wherein the DNA sequence encoding the chloroplast transit peptide comprises SEQ ID NO:12.

3. The recombinant DNA molecule of claim 1, wherein the DNA sequence encoding dicamba monooxygenase encodes a polypeptide selected from the group consisting of SEQ ID NOs: 26, 28, 32, 34, 36, 38, and 40.

4. The recombinant DNA molecule of claim 3, wherein the DNA sequence is selected from the group consisting of SEQ ID NOs: 25, 27, 31, 33, 35, 37, and 39.

5. A DNA construct comprising the DNA molecule of claim 1 operably linked to a promoter.

6. The DNA construct of claim 5, wherein the promoter is the PClSV promoter.

7. The construct of claim 5, wherein the promoter is functional in a plant cell.

8. A plant cell transformed with the DNA construct of claim 5.

9. The cell of claim 8, wherein the plant cell is a dicotyledonous plant cell.

10. The cell of claim 8, wherein the plant cell is a monocotyledonous plant cell.

11. The cell of claim 8, wherein the plant cell is a soybean, cotton, maize, or rapeseed plant cell.

12. A plant tissue culture comprising the cell of claim 8.

13. The plant tissue culture of claim 12, comprising a dicotyledonous plant cell.

14. The plant tissue culture of claim 12, comprising a monocotyledonous plant cell.

15. The plant tissue culture of claim 12, comprising a soybean, cotton, maize, or rapeseed plant cell.

16. A transgenic plant transformed with the DNA construct of claim 5.

17. The transgenic plant of claim 16, wherein the plant is a dicotyledonous plant.

18. The transgenic plant of claim 16, wherein the plant is a monocotyledonous plant.

19. The transgenic plant of claim 16, wherein the plant is a soybean, cotton, maize or rapeseed plant.

20. A method for producing a dicamba tolerant plant comprising introducing the construct of claim 5 into a plant cell and regenerating a plant therefrom that comprises the construct of claim 5.

21. The method of claim 20, further comprising producing a dicamba tolerant plant by crossing a parent plant with itself or with a second plant, wherein the parent plant and/or the second plant comprises the DNA construct and the dicamba tolerant plant inherits the DNA construct from said parent plant and/or the second plant.

22. A method for expressing dicamba monooxygenase in a plant cell comprising growing a plant comprising a nucleic acid construct comprising a nucleotide sequence encoding a pea Rubisco small subunit chloroplast transit peptide (CTP) of SEQ ID NO:1 operably linked to a nucleotide sequence encoding dicamba monooxygenase, thereby expressing the dicamba monooxygenase.

23. A method for controlling weed growth in a crop growing environment comprising a plant of claim 16 or a seed thereof, comprising applying to the crop growing environment an amount of dicamba herbicide effective to control weed growth.

24. The method of claim 23, wherein the dicamba herbicide is applied over the top to the crop growing environment.

25. The method of claim 23, wherein the amount of dicamba herbicide does not damage said plant or seed thereof and damages a plant of the same genotype as the plant, but lacking the construct.

26. A method for producing food, feed, or an industrial product comprising:
   a) obtaining the plant of claim 16 or a part thereof; and
   b) preparing the food, feed, fiber, or industrial product from the plant or part thereof.

27. The method of claim 26, wherein the food or feed is grain, meal, oil, starch, flour, or protein.

28. The method of claim 26, wherein the industrial product is biofuel, fiber, industrial chemicals, a pharmaceutical, or nutraceutical.

29. A dicamba tolerant seed comprising a DNA encoding a chloroplast transit peptide of SEQ ID NO:1 operably linked to a DNA encoding dicamba monooxygenase.

30. The dicamba tolerant seed of claim 29, wherein the DNA encoding the chloroplast transit peptide comprises SEQ ID NO:12.

31. The dicamba tolerant seed of claim 29, wherein the DNA encodes dicamba monooxygenase comprising a sequence selected from the group consisting of SEQ ID NOS: 26, 28, 32, 34, 36, 38, and 40.

32. A method for improving standability of a monocot plant comprising: a) growing a plant or seed produced by the method of claim 21; and b) treating the plant or seed with dicamba.

33. The method of claim 32, further comprising: c) measuring a standability-related parameter selected from the group consisting of brace root number, shape, length, or structure; percent lodging; and yield.

* * * * *

SEQUENCE LISTING

```
<160> NUMBER OF SEQ ID NOS: 41

<210> SEQ ID NO 1
<211> LENGTH: 84
<212> TYPE: PRT
<213> ORGANISM: Pisum sativum

<400> SEQUENCE: 1

Met Ala Ser Met Ile Ser Ser Ser Ala Val Thr Thr Val Ser Arg Ala
1               5                   10                  15

Ser Arg Gly Gln Ser Ala Ala Met Ala Pro Phe Gly Gly Leu Lys Ser
            20                  25                  30
```

```
Met Thr Gly Phe Pro Val Arg Lys Val Asn Thr Asp Ile Thr Ser Ile
            35                  40                  45

Thr Ser Asn Gly Gly Arg Val Lys Cys Met Gln Val Trp Pro Pro Ile
     50                  55                  60

Gly Lys Lys Lys Phe Glu Thr Leu Ser Tyr Leu Pro Pro Leu Thr Arg
 65                  70                  75                  80

Asp Ser Arg Ala

<210> SEQ ID NO 2
<211> LENGTH: 57
<212> TYPE: PRT
<213> ORGANISM: Pisum sativum

<400> SEQUENCE: 2

Met Ala Ser Met Ile Ser Ser Ala Val Thr Thr Val Ser Arg Ala
 1               5                  10                  15

Ser Arg Gly Gln Ser Ala Ala Met Ala Pro Phe Gly Gly Leu Lys Ser
            20                  25                  30

Met Thr Gly Phe Pro Val Arg Lys Val Asn Thr Asp Ile Thr Ser Ile
            35                  40                  45

Thr Ser Asn Gly Gly Arg Val Lys Cys
     50                  55

<210> SEQ ID NO 3
<211> LENGTH: 85
<212> TYPE: PRT
<213> ORGANISM: Arabidopsis thaliana

<400> SEQUENCE: 3

Met Ala Ser Ser Met Leu Ser Ser Ala Thr Met Val Ala Ser Pro Ala
 1               5                  10                  15

Gln Ala Thr Met Val Ala Pro Phe Asn Gly Leu Lys Ser Ser Ala Ala
            20                  25                  30

Phe Pro Ala Thr Arg Lys Ala Asn Asn Asp Ile Thr Ser Ile Thr Ser
            35                  40                  45

Asn Gly Gly Arg Val Asn Cys Met Gln Val Trp Pro Pro Ile Glu Lys
     50                  55                  60

Lys Lys Phe Glu Thr Leu Ser Tyr Leu Pro Asp Leu Thr Asp Ser Gly
 65                  70                  75                  80

Gly Arg Val Asn Cys
                85

<210> SEQ ID NO 4
<211> LENGTH: 76
<212> TYPE: PRT
<213> ORGANISM: Arabidopsis thaliana

<400> SEQUENCE: 4

Met Ala Gln Val Ser Arg Ile Cys Asn Gly Val Gln Asn Pro Ser Leu
 1               5                  10                  15

Ile Ser Asn Leu Ser Lys Ser Ser Gln Arg Lys Ser Pro Leu Ser Val
            20                  25                  30

Ser Leu Lys Thr Gln Gln His Pro Arg Ala Tyr Pro Ile Ser Ser Ser
            35                  40                  45

Trp Gly Leu Lys Lys Ser Gly Met Thr Leu Ile Gly Ser Glu Leu Arg
     50                  55                  60

Pro Leu Lys Val Met Ser Ser Val Ser Thr Ala Cys
 65                  70                  75
```

```
<210> SEQ ID NO 5
<211> LENGTH: 76
<212> TYPE: PRT
<213> ORGANISM: Arabidopsis thaliana

<400> SEQUENCE: 5

Met Ala Gln Val Ser Arg Ile Cys Asn Gly Val Gln Asn Pro Ser Leu
1               5                   10                  15

Ile Ser Asn Leu Ser Lys Ser Ser Gln Arg Lys Ser Pro Leu Ser Val
            20                  25                  30

Ser Leu Lys Thr Gln Gln His Pro Arg Ala Tyr Pro Ile Ser Ser Ser
        35                  40                  45

Trp Gly Leu Lys Lys Ser Gly Met Thr Leu Ile Gly Ser Glu Leu Arg
    50                  55                  60

Pro Leu Lys Val Met Ser Ser Val Ser Thr Ala Cys
65                  70                  75

<210> SEQ ID NO 6
<211> LENGTH: 72
<212> TYPE: PRT
<213> ORGANISM: Petunia x hybrida

<400> SEQUENCE: 6

Met Ala Gln Ile Asn Asn Met Ala Gln Gly Ile Gln Thr Leu Asn Pro
1               5                   10                  15

Asn Ser Asn Phe His Lys Pro Gln Val Pro Lys Ser Ser Phe Leu
            20                  25                  30

Val Phe Gly Ser Lys Lys Leu Lys Asn Ser Ala Asn Ser Met Leu Val
        35                  40                  45

Leu Lys Lys Asp Ser Ile Phe Met Gln Lys Phe Cys Ser Phe Arg Ile
    50                  55                  60

Ser Ala Ser Val Ala Thr Ala Cys
65                  70

<210> SEQ ID NO 7
<211> LENGTH: 69
<212> TYPE: PRT
<213> ORGANISM: Triticum aestivum

<400> SEQUENCE: 7

Met Ala Ala Leu Val Thr Ser Gln Leu Ala Thr Ser Gly Thr Val Leu
1               5                   10                  15

Ser Val Thr Asp Arg Phe Arg Arg Pro Gly Phe Gln Gly Leu Arg Pro
            20                  25                  30

Arg Asn Pro Ala Asp Ala Ala Leu Gly Met Arg Thr Val Gly Ala Ser
        35                  40                  45

Ala Ala Pro Lys Gln Ser Arg Lys Pro His Arg Phe Asp Arg Arg Cys
    50                  55                  60

Leu Ser Met Val Val
65

<210> SEQ ID NO 8
<211> LENGTH: 77
<212> TYPE: PRT
<213> ORGANISM: Oryza sativa
```

<400> SEQUENCE: 8

```
Met Ala Ala Leu Thr Thr Ser Gln Leu Ala Thr Ser Ala Thr Gly Phe
1               5                   10                  15

Gly Ile Ala Asp Arg Ser Ala Pro Ser Ser Leu Leu Arg His Gly Phe
            20                  25                  30

Gln Gly Leu Lys Pro Arg Ser Pro Ala Gly Gly Asp Ala Thr Ser Leu
        35                  40                  45

Ser Val Thr Thr Ser Ala Arg Ala Thr Pro Lys Gln Gln Arg Ser Val
50                  55                  60

Gln Arg Gly Ser Arg Phe Pro Ser Val Val Cys
65                  70                  75
```

<210> SEQ ID NO 9
<211> LENGTH: 57
<212> TYPE: PRT
<213> ORGANISM: Nicotiana tabacum

<400> SEQUENCE: 9

```
Met Ala Ser Ser Val Leu Ser Ser Ala Ala Val Ala Thr Arg Ser Asn
1               5                   10                  15

Val Ala Gln Ala Asn Met Val Ala Pro Phe Thr Gly Leu Lys Ser Ala
            20                  25                  30

Ala Ser Phe Pro Val Ser Arg Lys Gln Asn Leu Asp Ile Thr Ser Ile
        35                  40                  45

Ala Ser Asn Gly Gly Arg Val Gln Cys
50                  55
```

<210> SEQ ID NO 10
<211> LENGTH: 65
<212> TYPE: PRT
<213> ORGANISM: Zea mays

<400> SEQUENCE: 10

```
Met Glu Ser Leu Ala Ala Thr Ser Val Phe Ala Pro Ser Arg Val Ala
1               5                   10                  15

Val Pro Ala Ala Arg Ala Leu Val Arg Ala Gly Thr Val Val Pro Thr
            20                  25                  30

Arg Arg Thr Ser Ser Arg Ser Gly Thr Ser Gly Val Lys Cys Ser Ala
        35                  40                  45

Ala Val Thr Pro Gln Ala Ser Pro Val Ile Ser Arg Ser Ala Ala Ala
50                  55                  60

Ala
65
```

<210> SEQ ID NO 11
<211> LENGTH: 72
<212> TYPE: PRT
<213> ORGANISM: Ruta graveolens

<400> SEQUENCE: 11

```
Met Gly Ala Ala Ala Thr Ser Met Gln Ser Leu Lys Phe Ser Asn Arg
1               5                   10                  15

Leu Val Pro Pro Ser Arg Arg Leu Ser Pro Val Pro Asn Asn Val Thr
            20                  25                  30

Cys Asn Asn Leu Pro Lys Ser Ala Ala Pro Val Arg Thr Val Lys Cys
        35                  40                  45
```

```
Cys Ala Ser Ser Trp Asn Ser Thr Ile Asn Gly Ala Ala Ala Thr Thr
 50                  55                  60

Asn Gly Ala Ser Ala Ala Ser Ser
 65                  70

<210> SEQ ID NO 12
<211> LENGTH: 252
<212> TYPE: DNA
<213> ORGANISM: Pisum Sativum

<400> SEQUENCE: 12
atggcttcta tgatatcctc ttccgctgtg acaacagtca gccgtgcctc tagggggcaa      60
tccgccgcaa tggctccatt cggcggcctc aaatccatga ctggattccc agtgaggaag     120
gtcaacactg acattacttc cattacaagc aatggtggaa gagtaaagtg catgcaggtg     180
tggcctccaa ttggaaagaa gaagtttgag actctttcct atttgccacc attgacgaga     240
gattcccggg cc                                                         252

<210> SEQ ID NO 13
<211> LENGTH: 171
<212> TYPE: DNA
<213> ORGANISM: Pisum sativum

<400> SEQUENCE: 13
atggcttcta tgatatcctc ttccgctgtg acaacagtca gccgtgcctc tagggggcaa      60
tccgccgcaa tggctccatt cggcggcctc aaatccatga ctggattccc agtgaggaag     120
gtcaacactg acattacttc cattacaagc aatggtggaa gagtaaagtg c              171

<210> SEQ ID NO 14
<211> LENGTH: 255
<212> TYPE: DNA
<213> ORGANISM: Arabidopsis thaliana

<400> SEQUENCE: 14
atggcttcct ctatgctctc ttccgctact atggttgcct ctccggctca ggccactatg      60
gtcgctcctt tcaacggact taagtcctcc gctgccttcc cagccacccg caaggctaac     120
aacgacatta cttccatcac aagcaacggc ggaagagtta actgtatgca ggtgtggcct     180
ccgattgaaa agaagaagtt tgagactctc tcttaccttc tgaccttac cgattccggt     240 ggtcgcgtca actgc                                                      255

<210> SEQ ID NO 15
<211> LENGTH: 228
<212> TYPE: DNA
<213> ORGANISM: Arabidopsis thaliana

<400> SEQUENCE: 15
atggcgcaag ttagcagaat ctgcaatggt gtgcagaacc catctcttat ctccaatctc      60
tcgaaatcca gtcaacgcaa atctccctta tcggtttctc tgaagacgca gcagcatcca     120
cgagcttatc cgatttcgtc gtcgtgggga ttgaagaaga gtgggatgac gttaattggc     180
tctgagcttc gtcctcttaa ggtcatgtct ctgtttcca cggcgtgc                   228

<210> SEQ ID NO 16
<211> LENGTH: 228
<212> TYPE: DNA
<213> ORGANISM: Artificial sequence
<220> FEATURE:
<223> OTHER INFORMATION: Synthetic codon optimized CTP2 coding sequence
```

```
<400> SEQUENCE: 16
atggcgcaag ttagcagaat ctgcaatggt gtgcagaacc catctcttat ctccaatctc    60
tcgaaatcca gtcaacgcaa atctccctta tcggtttctc tgaagacgca gcagcatcca   120
cgagcttatc cgatttcgtc gtcgtgggga ttgaagaaga gtgggatgac gttaattggc   180
tctgagcttc gtcctcttaa ggtcatgtct tctgttttcca cggcgtgc               228

<210> SEQ ID NO 17
<211> LENGTH: 216
<212> TYPE: DNA
<213> ORGANISM: Artificial sequence
<220> FEATURE:
<223> OTHER INFORMATION: Synthetic codon optimized CTP4 coding sequence

<400> SEQUENCE: 17
atggcccaga tcaacaacat ggcccagggc atccagaccc tgaaccctaa ctctaacttc    60
cacaagccgc aagtgcccaa gtctagctcc ttcctcgtgt tcggctccaa gaagctcaag   120
aatagcgcca attccatgct ggtcctgaag aaagactcga tcttcatgca gaagttctgc   180
tcctttcgca tcagtgcttc ggttgcgact gcctgc                             216

<210> SEQ ID NO 18
<211> LENGTH: 207
<212> TYPE: DNA
<213> ORGANISM: Artificial sequence
<220> FEATURE:
<223> OTHER INFORMATION: Synthetic codon optimized TaWaxy CTP coding
      sequence

<400> SEQUENCE: 18
atggcggcac tggtgaccct ccagctcgcg acaagcggca ccgtcctgtc ggtgacggac    60
cgcttccggc gtcccggctt ccagggactg aggccacgga acccagccga tgccgctctc   120
gggatgagga cggtgggcgc gtccgcggct cccaagcaga gcaggaagcc acaccgtttc   180
gaccgccggt gcttgagcat ggtcgtc                                       207

<210> SEQ ID NO 19
<211> LENGTH: 231
<212> TYPE: DNA
<213> ORGANISM: Oryza sativa

<400> SEQUENCE: 19
atggcggctc tcaccacgtc ccagctcgcc acctcggcca ccggcttcgg catcgccgac    60
aggtcggcgc cgtcgtcgct gctccgccac gggttccagg gctcaagcc ccgcagcccc    120 gccggcggcg acgcgacgtc gctcagcgtg acgaccagcg cgcgcgcgac gcccaagcag   180
cagcggtcgg tgcagcgtgg cagccggagg ttcccctccg tcgtcgtgtg c             231

<210> SEQ ID NO 20
<211> LENGTH: 171
<212> TYPE: DNA
<213> ORGANISM: Nicotiana tabacum

<400> SEQUENCE: 20
atggcttcct cagttctttc ctctgcagca gttgccaccc gcagcaatgt tgctcaagct    60
aacatggttg cacctttcac tggccttaag tcagctgcct cattcccctgt ttcaaggaag  120 caaaaccttg acatcactc cattgccagc aacggcggaa gagtgcaatg c             171
```

<210> SEQ ID NO 21
<211> LENGTH: 195
<212> TYPE: DNA
<213> ORGANISM: Zea mays

<400> SEQUENCE: 21

| | | | | | | |
|---|---|---|---|---|---|---|
| atggaatccc | tagccgccac | ctccgtgttc | gcgccctccc | gcgtcgccgt | cccggcggcg | 60 |
| cgggccctgg | ttagggcggg | gacggtggta | ccaaccaggc | ggacgagcag | ccggagcgga | 120 |
| accagcgggg | tgaaatgctc | tgctgccgtg | acgccgcagg | cgagcccagt | gattagcagg | 180 |
| agcgctgcgg | cggcc | | | | | 195 |

<210> SEQ ID NO 22
<211> LENGTH: 216
<212> TYPE: DNA
<213> ORGANISM: Ruta graveolens

<400> SEQUENCE: 22

| | | | | | | |
|---|---|---|---|---|---|---|
| atgggtgcag | cggcaacgtc | gatgcaatcc | cttaaattct | ccaaccgtct | ggtcccaccc | 60 |
| agtcgccgtc | tgtctccggt | tccgaacaat | gtcacctgca | ataacctccc | caagtctgca | 120 |
| gctcccgtcc | ggacagtcaa | atgctgcgct | tcttcctgga | acagtaccat | caacggcgcg | 180 |
| gccgccacga | ccaacggtgc | gtccgccgcc | agtagc | | | 216 |

<210> SEQ ID NO 23
<211> LENGTH: 1023
<212> TYPE: DNA
<213> ORGANISM: Artificial sequence
<220> FEATURE:
<223> OTHER INFORMATION: Synthetic DMO-Cat(A) coding sequence

<400> SEQUENCE: 23

| | | | | | | |
|---|---|---|---|---|---|---|
| atggccactt | tcgttagaaa | cgcttggtac | gttgctgcac | ttcctgagga | gttgagcgag | 60 |
| aagcctctag | gaagaactat | cctcgatact | ccactagctc | tctatcgtca | acctgacgga | 120 |
| gttgtcgctg | ccctgcttga | tatttgtccg | catcgcttcg | ctccgttgag | tgacggtatt | 180 |
| ctagtcaacg | gacatctcca | gtgtccatat | cacggtctgg | aatttgacgg | aggtggccag | 240 |
| tgtgtccaca | acccgcacgg | caacggagcc | cgccctgctt | ctctgaacgt | gcgatcattc | 300 |
| cctgtcgtgg | aaagagacgc | attgatctgg | atctgccctg | gagatccagc | actcgcagat | 360 |
| cccggtgcta | tccctgactt | tgggtgtcgt | gttgatccag | cttaccgtac | tgtcggaggt | 420 |
| tacggtcacg | tggactgcaa | ctacaagctc | cttgtggata | acctcatgga | tcttggacac | 480 |
| gctcagtacg | tgcaccgcgc | taacgcccaa | acagacgcct | tcgatagact | tgagcgtgag | 540 |
| gtgatcgttg | gcgacggcga | gatccaggcg | ctcatgaaga | tccctggtgg | cacaccctca | 600 |
| gttctcatgg | ctaagttctt | gcgtggtgct | aacacaccag | ttgacgcctg | gaacgacatc | 660 |
| cggtggaata | aggtgtcggc | tatgctgaac | ttcatcgcgg | tcgcgccgga | agggacgccg | 720 |
| aaggagcagt | caatccactc | ccgaggaacc | catatcctta | ctcctgagac | cgaggcaagc | 780 |
| tgccattact | tcttcggtag | ttcccgcaac | ttcgtgtatg | acgatccaga | gatgacggt | 840 |
| gttctcagga | gctggcaagc | tcaagccctg | gtgaaggagg | acaaagtggt | cgttgaagct | 900 |
| atcgaaaggc | ggagggctta | cgtcgaagcg | aacgggatca | gacccgccat | gttgtcctgc | 960 |
| gacgaggcag | ccgtcagggt | atccagggag | attgagaagc | tcgaacaact | agaagcggcg | 1020 |
| tga | | | | | | 1023 |

```
<210> SEQ ID NO 24
<211> LENGTH: 340
<212> TYPE: PRT
<213> ORGANISM: Artificial sequence
<220> FEATURE:
<223> OTHER INFORMATION: Modified dicamba monooxygenase sequence:
      DMO-Cat(A)

<400> SEQUENCE: 24

Met Ala Thr Phe Val Arg Asn Ala Trp Tyr Val Ala Ala Leu Pro Glu
1               5                   10                  15

Glu Leu Ser Glu Lys Pro Leu Gly Arg Thr Ile Leu Asp Thr Pro Leu
            20                  25                  30

Ala Leu Tyr Arg Gln Pro Asp Gly Val Val Ala Ala Leu Leu Asp Ile
        35                  40                  45

Cys Pro His Arg Phe Ala Pro Leu Ser Asp Gly Ile Leu Val Asn Gly
    50                  55                  60

His Leu Gln Cys Pro Tyr His Gly Leu Glu Phe Asp Gly Gly Gly Gln
65                  70                  75                  80

Cys Val His Asn Pro His Gly Asn Gly Ala Arg Pro Ala Ser Leu Asn
                85                  90                  95

Val Arg Ser Phe Pro Val Val Glu Arg Asp Ala Leu Ile Trp Ile Cys
            100                 105                 110

Pro Gly Asp Pro Ala Leu Ala Asp Pro Gly Ala Ile Pro Asp Phe Gly
        115                 120                 125

Cys Arg Val Asp Pro Ala Tyr Arg Thr Val Gly Gly Tyr Gly His Val
    130                 135                 140

Asp Cys Asn Tyr Lys Leu Leu Val Asp Asn Leu Met Asp Leu Gly His
145                 150                 155                 160

Ala Gln Tyr Val His Arg Ala Asn Ala Gln Thr Asp Ala Phe Asp Arg
                165                 170                 175

Leu Glu Arg Glu Val Ile Val Gly Asp Gly Glu Ile Gln Ala Leu Met
            180                 185                 190

Lys Ile Pro Gly Gly Thr Pro Ser Val Leu Met Ala Lys Phe Leu Arg
        195                 200                 205

Gly Ala Asn Thr Pro Val Asp Ala Trp Asn Asp Ile Arg Trp Asn Lys
    210                 215                 220

Val Ser Ala Met Leu Asn Phe Ile Ala Val Ala Pro Glu Gly Thr Pro
225                 230                 235                 240

Lys Glu Gln Ser Ile His Ser Arg Gly Thr His Ile Leu Thr Pro Glu
                245                 250                 255

Thr Glu Ala Ser Cys His Tyr Phe Phe Gly Ser Ser Arg Asn Phe Gly
            260                 265                 270

Ile Asp Asp Pro Glu Met Asp Gly Val Leu Arg Ser Trp Gln Ala Gln
        275                 280                 285

Ala Leu Val Lys Glu Asp Lys Val Val Glu Ala Ile Glu Arg Arg
    290                 295                 300

Arg Ala Tyr Val Glu Ala Asn Gly Ile Arg Pro Ala Met Leu Ser Cys
305                 310                 315                 320

Asp Glu Ala Ala Val Arg Val Ser Arg Glu Ile Glu Lys Leu Glu Gln
                325                 330                 335

Leu Glu Ala Ala
        340
```

<210> SEQ ID NO 25
<211> LENGTH: 1023
<212> TYPE: DNA
<213> ORGANISM: Artificial sequence
<220> FEATURE:
<223> OTHER INFORMATION: Synthetic DMO-Cat(L) coding sequence

<400> SEQUENCE: 25

```
atgctcactt tcgttagaaa cgcttggtac gttgctgcac ttcctgagga gttgagcgag    60
aagcctctag gaagaactat cctcgatact ccactagctc tctatcgtca acctgacgga   120
gttgtcgctg ccctgcttga tatttgtccg catcgcttcg ctccgttgag tgacggtatt   180
ctagtcaacg gacatctcca gtgtccatat cacggtctgg aatttgacgg aggtggccag   240
tgtgtccaca acccgcacgg caacggagcc cgccctgctt ctctgaacgt gcgatcattc   300
cctgtcgtgg aaagagacgc attgatctgg atctgccctg gagatccagc actcgcagat   360
cccggtgcta tccctgactt tgggtgtcgt gttgatccag cttaccgtac tgtcggaggt   420
tacggtcacg tggactgcaa ctacaagctc cttgtggata acctcatgga tcttggacac   480
gctcagtacg tgcaccgcgc taacgcccaa acagacgcct tcgatagact tgagcgtgag   540
gtgatcgttg gcgacggcga gatccaggcg ctcatgaaga tccctggtgg cacaccctca   600
gttctcatgg ctaagttctt gcgtggtgct aacacaccag ttgacgcctg aacgacatc   660
cggtggaata aggtgtcggc tatgctgaac ttcatcgcgg tcgcgccgga agggacgccg   720
aaggagcagt caatccactc ccgaggaacc catatcctta ctcctgagac cgaggcaagc   780
tgccattact tcttcggtag ttcccgcaac ttcggtatag acgatccaga gatggacggt   840
gttctcagga gctggcaagc tcaagccctg gtgaaggagg acaaagtggt cgttgaagct   900
atcgaaaggc ggagggctta cgtcgaagcg aacgggatca gacccgccat gttgtcctgc   960
gacgaggcag ccgtcagggt atccagggag attgagaagc tcgaacaact agaagcggcg  1020
tga                                                                1023
```

<210> SEQ ID NO 26
<211> LENGTH: 340
<212> TYPE: PRT
<213> ORGANISM: Artificial sequence
<220> FEATURE:
<223> OTHER INFORMATION: Modified dicamba monooxygenase sequence:
      DMO-Cat(L)

<400> SEQUENCE: 26

```
Met Leu Thr Phe Val Arg Asn Ala Trp Tyr Val Ala Ala Leu Pro Glu
1               5                   10                  15

Glu Leu Ser Glu Lys Pro Leu Gly Arg Thr Ile Leu Asp Thr Pro Leu
            20                  25                  30

Ala Leu Tyr Arg Gln Pro Asp Gly Val Val Ala Ala Leu Leu Asp Ile
        35                  40                  45

Cys Pro His Arg Phe Ala Pro Leu Ser Asp Gly Ile Leu Val Asn Gly
    50                  55                  60

His Leu Gln Cys Pro Tyr His Gly Leu Glu Phe Asp Gly Gly Gly Gln
65                  70                  75                  80

Cys Val His Asn Pro His Gly Asn Gly Ala Arg Pro Ala Ser Leu Asn
                85                  90                  95

Val Arg Ser Phe Pro Val Val Glu Arg Asp Ala Leu Ile Trp Ile Cys
            100                 105                 110

Pro Gly Asp Pro Ala Leu Ala Asp Pro Gly Ala Ile Pro Asp Phe Gly
        115                 120                 125
```

```
Cys Arg Val Asp Pro Ala Tyr Arg Thr Val Gly Gly Tyr Gly His Val
        130                 135                 140
Asp Cys Asn Tyr Lys Leu Leu Val Asp Asn Leu Met Asp Leu Gly His
145                 150                 155                 160
Ala Gln Tyr Val His Arg Ala Asn Ala Gln Thr Asp Ala Phe Asp Arg
                165                 170                 175
Leu Glu Arg Glu Val Ile Val Gly Asp Gly Glu Ile Gln Ala Leu Met
            180                 185                 190
Lys Ile Pro Gly Gly Thr Pro Ser Val Leu Met Ala Lys Phe Leu Arg
        195                 200                 205
Gly Ala Asn Thr Pro Val Asp Ala Trp Asn Asp Ile Arg Trp Asn Lys
    210                 215                 220
Val Ser Ala Met Leu Asn Phe Ile Ala Val Ala Pro Glu Gly Thr Pro
225                 230                 235                 240
Lys Glu Gln Ser Ile His Ser Arg Gly Thr His Ile Leu Thr Pro Glu
                245                 250                 255
Thr Glu Ala Ser Cys His Tyr Phe Phe Gly Ser Ser Arg Asn Phe Gly
            260                 265                 270
Ile Asp Asp Pro Glu Met Asp Gly Val Leu Arg Ser Trp Gln Ala Gln
        275                 280                 285
Ala Leu Val Lys Glu Asp Lys Val Val Glu Ala Ile Glu Arg Arg
    290                 295                 300
Arg Ala Tyr Val Glu Ala Asn Gly Ile Arg Pro Ala Met Leu Ser Cys
305                 310                 315                 320
Asp Glu Ala Ala Val Arg Val Ser Arg Glu Ile Glu Lys Leu Glu Gln
                325                 330                 335
Leu Glu Ala Ala
        340

<210> SEQ ID NO 27
<211> LENGTH: 1023
<212> TYPE: DNA
<213> ORGANISM: Artificial sequence
<220> FEATURE:
<223> OTHER INFORMATION: Synthetic DMO-Wat(L) coding sequence

<400> SEQUENCE: 27
atgctcactt tcgttagaaa cgcttggtac gttgctgcac ttcctgagga gttgagcgag      60
aagcctctag gaagaactat cctcgatact ccactagctc tctatcgtca acctgacgga     120
gttgtcgctg ccctgcttga tatttgtccg catcgcttcg ctccgttgag tgacggtatt     180
ctagtcaacg gacatctcca gtgtccatat cacggtctgg aatttgacgg aggtggccag     240
tgtgtccaca acccgcacgg caacggagcc cgccctgctt ctctgaacgt gcgatcattc     300
cctgtcgtgg aaagagacgc attgatctgg atctggcctg gagatccagc actcgcagat     360
cccggtgcta tccctgactt tgggtgtcgt gttgatccag cttaccgtac tgtcggaggt     420
tacggtcacg tggactgcaa ctacaagctc cttgtggata acctcatgga tcttggacac     480
gctcagtacg tgcaccgcgc taacgcccaa acagacgcct cgatagact tgagcgtgag     540 gtgatcgttg gcgacggcga gatccaggcg ctcatgaaga tccctggtgg cacaccctca     600
gttctcatgg ctaagttctt gcgtggtgct aacacaccag ttgacgcctg gaacgacatc     660
cggtggaata aggtgtcggc tatgctgaac ttcatcgcgg tcgcgccgga agggacgccg     720
aaggagcagt caatccactc ccgaggaacc catatcctta ctcctgagac cgaggcaagc     780
tgccattact tcttcggtag ttcccgcaac ttcggtatag acgatccaga gatggacggt     840
```

-continued

```
gttctcagga gctggcaagc tcaagccctg gtgaaggagg acaaagtggt cgttgaagct    900
atcgaaaggc ggagggctta cgtcgaagcg aacgggatca gacccgccat gttgtcctgc    960
gacgaggcag ccgtcagggt atccaggag attgagaagc tcgaacaact agaagcggcg   1020
tga                                                                  1023
```

<210> SEQ ID NO 28
<211> LENGTH: 340
<212> TYPE: PRT
<213> ORGANISM: Artificial sequence
<220> FEATURE:
<223> OTHER INFORMATION: Modified dicamba monooxygenase sequence:
      DMO-Wat(L)

<400> SEQUENCE: 28

```
Met Leu Thr Phe Val Arg Asn Ala Trp Tyr Val Ala Ala Leu Pro Glu
1               5                   10                  15

Glu Leu Ser Glu Lys Pro Leu Gly Arg Thr Ile Leu Asp Thr Pro Leu
            20                  25                  30

Ala Leu Tyr Arg Gln Pro Asp Gly Val Val Ala Ala Leu Leu Asp Ile
        35                  40                  45

Cys Pro His Arg Phe Ala Pro Leu Ser Asp Gly Ile Leu Val Asn Gly
    50                  55                  60

His Leu Gln Cys Pro Tyr His Gly Leu Glu Phe Asp Gly Gly Gly Gln
65                  70                  75                  80

Cys Val His Asn Pro His Gly Asn Gly Ala Arg Pro Ala Ser Leu Asn
                85                  90                  95

Val Arg Ser Phe Pro Val Val Glu Arg Asp Ala Leu Ile Trp Ile Trp
            100                 105                 110

Pro Gly Asp Pro Ala Leu Ala Asp Pro Gly Ala Ile Pro Asp Phe Gly
        115                 120                 125

Cys Arg Val Asp Pro Ala Tyr Arg Thr Val Gly Gly Tyr Gly His Val
    130                 135                 140

Asp Cys Asn Tyr Lys Leu Leu Val Asp Asn Leu Met Asp Leu Gly His
145                 150                 155                 160

Ala Gln Tyr Val His Arg Ala Asn Ala Gln Thr Asp Ala Phe Asp Arg
                165                 170                 175

Leu Glu Arg Glu Val Ile Val Gly Asp Gly Glu Ile Gln Ala Leu Met
            180                 185                 190

Lys Ile Pro Gly Gly Thr Pro Ser Val Leu Met Ala Lys Phe Leu Arg
        195                 200                 205

Gly Ala Asn Thr Pro Val Asp Ala Trp Asn Asp Ile Arg Trp Asn Lys
    210                 215                 220

Val Ser Ala Met Leu Asn Phe Ile Ala Val Ala Pro Glu Gly Thr Pro
225                 230                 235                 240

Lys Glu Gln Ser Ile His Ser Arg Gly Thr His Ile Leu Thr Pro Glu
                245                 250                 255

Thr Glu Ala Ser Cys His Tyr Phe Phe Gly Ser Ser Arg Asn Phe Gly
            260                 265                 270

Ile Asp Asp Pro Glu Met Asp Gly Val Leu Arg Ser Trp Gln Ala Gln
        275                 280                 285

Ala Leu Val Lys Glu Asp Lys Val Val Glu Ala Ile Glu Arg Arg
    290                 295                 300

Arg Ala Tyr Val Glu Ala Asn Gly Ile Arg Pro Ala Met Leu Ser Cys
305                 310                 315                 320
```

-continued

Asp Glu Ala Ala Val Arg Val Ser Arg Glu Ile Glu Lys Leu Glu Gln
            325                 330                 335

Leu Glu Ala Ala
            340

<210> SEQ ID NO 29
<211> LENGTH: 1023
<212> TYPE: DNA
<213> ORGANISM: Artificial sequence
<220> FEATURE:
<223> OTHER INFORMATION: Synthetic DMO-Cnat(A) coding sequence

<400> SEQUENCE: 29
atggccacct tcgtccgcaa tgcctggtat gtggcggcgc tgcccgagga actgtccgaa      60
aagccgctcg gccggacgat tctcgacaca ccgctcgcgc tctaccgcca gcccgacggt     120
gtggtcgcgg cgctgctcga catctgtccg caccgcttcg cgccgctgag cgacggcatc     180
ctcgtcaacg gccatctcca atgccccta t cacgggctgg aattcgatgg cggcgggcag     240
tgcgtcccata acccgcacgg caatggcgcc cgcccggctt cgctcaacgt ccgctccttc     300
ccggtggtgg agcgcgacgc gctgatctgg atctgtcccg cgatccggc gctggccgat     360
cctggggcga tccccgactt cggctgccgc gtcgatcccg cctatcggac cgtcggcggc     420
tatgggcatg tcgactgcaa ctacaagctg ctggtcgaca acctgatgga cctcggccac     480
gcccaatatg tccatcgcgc caacgcccag accgacgcct tcgaccggct ggagcgcgag     540
gtgatcgtcg cgacggtga atacaggcg ctgatgaaga ttcccggcgg cacgccgagc     600
gtgctgatgg ccaagttcct cgcgggcgcc aatacccccg tcgacgcttg gaacgacatc     660
cgctggaaca aggtgagcgc gatgctcaac ttcatcgcgg tggcgccgga aggcaccccg     720
aaggagcaga gcatccactc gcgcggtacc catatcctga ccccgagac ggaggcgagc     780
tgccattatt tcttcggctc ctcgcgcaat ttcggcatcg acgatccgga gatgacggc     840
gtgctgcgca gctggcaggc tcaggcgctg gtcaaggagg acaaggtcgt cgtcgaggcg     900
atcgagcgcc gccgcgccta tgtcgaggcg aatggcatcc gcccggcgat gctgtcgtgc     960
gacgaagccg cagtccgtgt cagccgcgag atcgagaagc ttgagcagct cgaagccgcc    1020
tga                                                                 1023

<210> SEQ ID NO 30
<211> LENGTH: 340
<212> TYPE: PRT
<213> ORGANISM: Artificial sequence
<220> FEATURE:
<223> OTHER INFORMATION: Modified dicamba monooxygenase sequence:
      DMO-Cnat(A)

<400> SEQUENCE: 30

Met Ala Thr Phe Val Arg Asn Ala Trp Tyr Val Ala Ala Leu Pro Glu
1               5                   10                  15

Glu Leu Ser Glu Lys Pro Leu Gly Arg Thr Ile Leu Asp Thr Pro Leu
            20                  25                  30

Ala Leu Tyr Arg Gln Pro Asp Gly Val Val Ala Ala Leu Leu Asp Ile
        35                  40                  45

Cys Pro His Arg Phe Ala Pro Leu Ser Asp Gly Ile Leu Val Asn Gly
    50                  55                  60

His Leu Gln Cys Pro Tyr His Gly Leu Glu Phe Asp Gly Gly Gly Gln
65                  70                  75                  80

```
Cys Val His Asn Pro His Gly Asn Gly Ala Arg Pro Ala Ser Leu Asn
            85                  90                  95

Val Arg Ser Phe Pro Val Val Glu Arg Asp Ala Leu Ile Trp Ile Cys
        100                 105                 110

Pro Gly Asp Pro Ala Leu Ala Asp Pro Gly Ala Ile Pro Asp Phe Gly
    115                 120                 125

Cys Arg Val Asp Pro Ala Tyr Arg Thr Val Gly Gly Tyr Gly His Val
130                 135                 140

Asp Cys Asn Tyr Lys Leu Leu Val Asp Asn Leu Met Asp Leu Gly His
145                 150                 155                 160

Ala Gln Tyr Val His Arg Ala Asn Ala Gln Thr Asp Ala Phe Asp Arg
                165                 170                 175

Leu Glu Arg Glu Val Ile Val Gly Asp Gly Glu Ile Gln Ala Leu Met
            180                 185                 190

Lys Ile Pro Gly Gly Thr Pro Ser Val Leu Met Ala Lys Phe Leu Arg
        195                 200                 205

Gly Ala Asn Thr Pro Val Asp Ala Trp Asn Asp Ile Arg Trp Asn Lys
    210                 215                 220

Val Ser Ala Met Leu Asn Phe Ile Ala Val Ala Pro Glu Gly Thr Pro
225                 230                 235                 240

Lys Glu Gln Ser Ile His Ser Arg Gly Thr His Ile Leu Thr Pro Glu
                245                 250                 255

Thr Glu Ala Ser Cys His Tyr Phe Phe Gly Ser Ser Arg Asn Phe Gly
            260                 265                 270

Ile Asp Asp Pro Glu Met Asp Gly Val Leu Arg Ser Trp Gln Ala Gln
        275                 280                 285

Ala Leu Val Lys Glu Asp Lys Val Val Val Ala Ile Glu Arg Arg
    290                 295                 300

Arg Ala Tyr Val Glu Ala Asn Gly Ile Arg Pro Ala Met Leu Ser Cys
305                 310                 315                 320

Asp Glu Ala Ala Val Arg Val Ser Arg Glu Ile Glu Lys Leu Glu Gln
                325                 330                 335

Leu Glu Ala Ala
            340

<210> SEQ ID NO 31
<211> LENGTH: 1023
<212> TYPE: DNA
<213> ORGANISM: Artificial sequence
<220> FEATURE:
<223> OTHER INFORMATION: Synthetic DMO-Wat(A) coding sequence

<400> SEQUENCE: 31
atggccactt cgttagaaa cgcttggtac gttgctgcac ttcctgagga gttgagcgag      60
aagcctctag gaagaactat cctcgatact ccactagctc tctatcgtca acctgacgga    120
gttgtcgctg ccctgcttga tatttgtccg catcgcttcg ctccgttgag tgacggtatt    180
ctagtcaacg gacatctcca gtgtccatat cacggtctgg aatttgacgg aggtggccag    240
tgtgtccaca cccgcacgg caacggagcc cgccctgctt ctctgaacgt gcgatcattc    300
cctgtcgtgg aaagagacgc attgatctgg atctggcctg gagatccagc actcgcagat    360
cccggtgcta tccctgactt tgggtgtcgt gttgatccag cttaccgtac tgtcggaggt    420
tacggtcacg tggactgcaa ctacaagctc cttgtggata acctcatgga tcttggacac    480
gctcagtacg tgcaccgcgc taacgcccaa acagacgcct tcgatagact tgagcgtgag    540
```

-continued

```
gtgatcgttg gcgacggcga gatccaggcg ctcatgaaga tccctggtgg cacaccctca    600
gttctcatgg ctaagttctt gcgtggtgct aacacaccag ttgacgcctg gaacgacatc    660
cggtggaata aggtgtcggc tatgctgaac ttcatcgcgg tcgcgccgga agggacgccg    720
aaggagcagt caatccactc ccgaggaacc catatcctta ctcctgagac cgaggcaagc    780
tgccattact tcttcggtag ttcccgcaac ttcggtatag acgatccaga gatggacggt    840
gttctcagga gctggcaagc tcaagccctg gtgaaggagg acaaagtggt cgttgaagct    900
atcgaaaggc ggagggctta cgtcgaagcg aacgggatca gaccgccat gttgtcctgc    960 gacgaggcag ccgtcagggt atccaggag attgagaagc tcgaacaact agaagcggcg   1020
tga                                                                1023
```

<210> SEQ ID NO 32
<211> LENGTH: 340
<212> TYPE: PRT
<213> ORGANISM: Artificial sequence
<220> FEATURE:
<223> OTHER INFORMATION: Modified dicamba monooxygenase sequence: DMO-Wat(A)

<400> SEQUENCE: 32

```
Met Ala Thr Phe Val Arg Asn Ala Trp Tyr Val Ala Ala Leu Pro Glu
1               5                   10                  15

Glu Leu Ser Glu Lys Pro Leu Gly Arg Thr Ile Leu Asp Thr Pro Leu
            20                  25                  30

Ala Leu Tyr Arg Gln Pro Asp Gly Val Val Ala Ala Leu Leu Asp Ile
        35                  40                  45

Cys Pro His Arg Phe Ala Pro Leu Ser Asp Gly Ile Leu Val Asn Gly
    50                  55                  60

His Leu Gln Cys Pro Tyr His Gly Leu Glu Phe Asp Gly Gly Gly Gln
65                  70                  75                  80

Cys Val His Asn Pro His Gly Asn Gly Ala Arg Pro Ala Ser Leu Asn
                85                  90                  95

Val Arg Ser Phe Pro Val Val Glu Arg Asp Ala Leu Ile Trp Ile Trp
            100                 105                 110

Pro Gly Asp Pro Ala Leu Ala Asp Pro Gly Ala Ile Pro Asp Phe Gly
        115                 120                 125

Cys Arg Val Asp Pro Ala Tyr Arg Thr Val Gly Gly Tyr Gly His Val
    130                 135                 140

Asp Cys Asn Tyr Lys Leu Leu Val Asp Asn Leu Met Asp Leu Gly His
145                 150                 155                 160

Ala Gln Tyr Val His Arg Ala Asn Ala Gln Thr Asp Ala Phe Asp Arg
                165                 170                 175

Leu Glu Arg Glu Val Ile Val Gly Asp Gly Glu Ile Gln Ala Leu Met
            180                 185                 190

Lys Ile Pro Gly Gly Thr Pro Ser Val Leu Met Ala Lys Phe Leu Arg
        195                 200                 205

Gly Ala Asn Thr Pro Val Asp Ala Trp Asn Asp Ile Arg Trp Asn Lys
    210                 215                 220

Val Ser Ala Met Leu Asn Phe Ile Ala Val Ala Pro Glu Gly Thr Pro
225                 230                 235                 240

Lys Glu Gln Ser Ile His Ser Arg Gly Thr His Ile Leu Thr Pro Glu
                245                 250                 255

Thr Glu Ala Ser Cys His Tyr Phe Phe Gly Ser Ser Arg Asn Phe Gly
            260                 265                 270
```

Ile Asp Asp Pro Glu Met Asp Gly Val Leu Arg Ser Trp Gln Ala Gln
            275                 280                 285

Ala Leu Val Lys Glu Asp Lys Val Val Glu Ala Ile Glu Arg Arg
        290                 295                 300

Arg Ala Tyr Val Glu Ala Asn Gly Ile Arg Pro Ala Met Leu Ser Cys
305                 310                 315                 320

Asp Glu Ala Ala Val Arg Val Ser Arg Glu Ile Glu Lys Leu Glu Gln
                325                 330                 335

Leu Glu Ala Ala
        340

<210> SEQ ID NO 33
<211> LENGTH: 1020
<212> TYPE: DNA
<213> ORGANISM: Pseudomonas maltophilia

<400> SEQUENCE: 33

```
atgaccttcg tccgcaatgc ctggtatgtg gcggcgctgc ccgaggaact gtccgaaaag    60
ccgctcggcc ggacgattct cgacacaccg ctcgcgctct accgccagcc cgacggtgtg   120
gtcgcggcgc tgctcgacat ctgtccgcac cgcttcgcgc cgctgagcga cggcatcctc   180
gtcaacggcc atctccaatg cccctatcac gggctggaat cgatggcgg cgggcagtgc    240
gtccataacc cgcacggcaa tggcgcccgc ccggcttcgc tcaacgtccg ctccttcccg   300
gtggtggagc gcgacgcgct gatctggatc tggcccggcg atccggcgct ggccgatcct   360
ggggcgatcc ccgacttcgg ctgccgcgtc gatcccgcct atcggaccgt cggcggctat   420
ggcatgtcg actgcaacta caagctgctg gtcgacaacc tgatggacct cggccacgcc    480
caatatgtcc atcgcgccaa cgcccagacc gacgccttcg accggctgga gcgcgaggtg   540
atcgtcggcg acggtgagat acaggcgctg atgaagattc ccggcggcac gccgagcgtg   600
ctgatggcca gttcctgcg cggcgccaat accccgtcg acgcttggaa cgacatccgc     660
tggaacaagg tgagcgcgat gctcaacttc atcgcggtgg cgccggaagg caccccgaag   720
gagcagagca tccactcgcg cggtacccat atcctgaccc ccgagacgga ggcgagctgc   780
cattatttct tcggctcctc gcgcaatttc ggcatcgacg atccggagat ggacggcgtg   840
ctgcgcagct ggcaggctca ggcgctggtc aaggaggaca aggtcgtcgt cgaggcgatc   900
gagcgccgcc gcgcctatgt cgaggcgaat ggcatccgcc cggcgatgct gtcgtgcgac   960
gaagccgcag tccgtgtcag ccgcgagatc gagaagcttg agcagctcga agccgcctga  1020
```

<210> SEQ ID NO 34
<211> LENGTH: 339
<212> TYPE: PRT
<213> ORGANISM: Pseudomonas maltophilia

<400> SEQUENCE: 34

Met Thr Phe Val Arg Asn Ala Trp Tyr Val Ala Ala Leu Pro Glu Glu
1               5                   10                  15

Leu Ser Glu Lys Pro Leu Gly Arg Thr Ile Leu Asp Thr Pro Leu Ala
            20                  25                  30

Leu Tyr Arg Gln Pro Asp Gly Val Val Ala Ala Leu Leu Asp Ile Cys
        35                  40                  45

Pro His Arg Phe Ala Pro Leu Ser Asp Gly Ile Leu Val Asn Gly His
    50                  55                  60

Leu Gln Cys Pro Tyr His Gly Leu Glu Phe Asp Gly Gly Gly Gln Cys
65                  70                  75                  80

Val His Asn Pro His Gly Asn Gly Ala Arg Pro Ala Ser Leu Asn Val
            85                  90                  95

Arg Ser Phe Pro Val Val Glu Arg Asp Ala Leu Ile Trp Ile Trp Pro
        100                 105                 110

Gly Asp Pro Ala Leu Ala Asp Pro Gly Ala Ile Pro Asp Phe Gly Cys
            115                 120                 125

Arg Val Asp Pro Ala Tyr Arg Thr Val Gly Tyr Gly His Val Asp
        130                 135                 140

Cys Asn Tyr Lys Leu Leu Val Asp Asn Leu Met Asp Leu Gly His Ala
145                 150                 155                 160

Gln Tyr Val His Arg Ala Asn Ala Gln Thr Asp Ala Phe Asp Arg Leu
                165                 170                 175

Glu Arg Glu Val Ile Val Gly Asp Gly Glu Ile Gln Ala Leu Met Lys
            180                 185                 190

Ile Pro Gly Gly Thr Pro Ser Val Leu Met Ala Lys Phe Leu Arg Gly
            195                 200                 205

Ala Asn Thr Pro Val Asp Ala Trp Asn Asp Ile Arg Trp Asn Lys Val
210                 215                 220

Ser Ala Met Leu Asn Phe Ile Ala Val Ala Pro Glu Gly Thr Pro Lys
225                 230                 235                 240

Glu Gln Ser Ile His Ser Arg Gly Thr His Ile Leu Thr Pro Glu Thr
                245                 250                 255

Glu Ala Ser Cys His Tyr Phe Phe Gly Ser Ser Arg Asn Phe Gly Ile
            260                 265                 270

Asp Asp Pro Glu Met Asp Gly Val Leu Arg Ser Trp Gln Ala Gln Ala
        275                 280                 285

Leu Val Lys Glu Asp Lys Val Val Val Glu Ala Ile Glu Arg Arg
    290                 295                 300

Ala Tyr Val Glu Ala Asn Gly Ile Arg Pro Ala Met Leu Ser Cys Asp
305                 310                 315                 320

Glu Ala Ala Val Arg Val Ser Arg Glu Ile Glu Lys Leu Glu Gln Leu
                325                 330                 335

Glu Ala Ala

<210> SEQ ID NO 35
<211> LENGTH: 1023
<212> TYPE: DNA
<213> ORGANISM: Artificial sequence
<220> FEATURE:
<223> OTHER INFORMATION: Synthetic DMO-Cnat(L) coding sequence

<400> SEQUENCE: 35
atgctcacct tcgtccgcaa tgcctggtat gtggcggcgc tgcccgagga actgtccgaa      60
aagccgctcg gccggacgat tctcgacaca ccgctcgcgc tctaccgcca gcccgacggt     120
gtggtcgcgg cgctgctcga catctgtccg caccgcttcg cgccgctgag cgacggcatc     180
ctcgtcaacg gccatctcca atgccccta cacgggctgg aattcgatgg cggcgggcag     240
tgcgtccata acccgcacgg caatggcgcc cgcccggctt cgctcaacgt ccgctccttc     300
ccggtggtgg agcgcgacgc gctgatctgg atctgtcccg gcgatccggc tctggccgat     360
cctggggcga tcccgacttc ggctgccgc gtcgatcccg cctatcggac cgtcggcggc     420
tatgggcatg tcgactgcaa ctacaagctg ctggtcgaca acctgatgga cctcggccac     480
gcccaatatg tccatcgcgc caacgcccag accgacgcct cgaccggct ggagcgcgag     540 gtgatcgtcg gcgacggtga gatacaggcg ctgatgaaga ttcccggcgg cacgccgagc     600

-continued

```
gtgctgatgg ccaagttcct gcgcggcgcc aataccccg tcgacgcttg aacgacatc    660 cgctggaaca aggtgagcgc gatgctcaac ttcatcgcgg tggcgccgga aggcaccccg    720
aaggagcaga gcatccactc gcgcggtacc catatcctga cccccgagac ggaggcgagc    780
tgccattatt tcttcggctc ctcgcgcaat ttcggcatcg acgatccgga gatggacggc    840
gtgctgcgca gctggcaggc tcaggcgctg gtcaaggagg acaaggtcgt cgtcgaggcg    900
atcgagcgcc gccgcgccta tgtcgaggcg aatggcatcc gccggcgat gctgtcgtgc    960 gacgaagccg cagtccgtgt cagccgcgag atcgagaagc ttgagcagct cgaagccgcc    1020
tga                                                                    1023
```

<210> SEQ ID NO 36
<211> LENGTH: 340
<212> TYPE: PRT
<213> ORGANISM: Artificial sequence
<220> FEATURE:
<223> OTHER INFORMATION: Modified dicamba monooxygenase sequence: DMO-Cnat(L)

<400> SEQUENCE: 36

```
Met Leu Thr Phe Val Arg Asn Ala Trp Tyr Val Ala Ala Leu Pro Glu
 1               5                  10                  15

Glu Leu Ser Glu Lys Pro Leu Gly Arg Thr Ile Leu Asp Thr Pro Leu
            20                  25                  30

Ala Leu Tyr Arg Gln Pro Asp Gly Val Val Ala Ala Leu Leu Asp Ile
        35                  40                  45

Cys Pro His Arg Phe Ala Pro Leu Ser Asp Gly Ile Leu Val Asn Gly
    50                  55                  60

His Leu Gln Cys Pro Tyr His Gly Leu Glu Phe Asp Gly Gly Gly Gln
65                  70                  75                  80

Cys Val His Asn Pro His Gly Asn Gly Ala Arg Pro Ala Ser Leu Asn
                85                  90                  95

Val Arg Ser Phe Pro Val Val Glu Arg Asp Ala Leu Ile Trp Ile Cys
            100                 105                 110

Pro Gly Asp Pro Ala Leu Ala Asp Pro Gly Ala Ile Pro Asp Phe Gly
        115                 120                 125

Cys Arg Val Asp Pro Ala Tyr Arg Thr Val Gly Gly Tyr Gly His Val
    130                 135                 140

Asp Cys Asn Tyr Lys Leu Leu Val Asp Asn Leu Met Asp Leu Gly His
145                 150                 155                 160

Ala Gln Tyr Val His Arg Ala Asn Ala Gln Thr Asp Ala Phe Asp Arg
                165                 170                 175

Leu Glu Arg Glu Val Ile Val Gly Asp Gly Glu Ile Gln Ala Leu Met
            180                 185                 190

Lys Ile Pro Gly Gly Thr Pro Ser Val Leu Met Ala Lys Phe Leu Arg
        195                 200                 205

Gly Ala Asn Thr Pro Val Asp Ala Trp Asn Asp Ile Arg Trp Asn Lys
    210                 215                 220

Val Ser Ala Met Leu Asn Phe Ile Ala Val Ala Pro Glu Gly Thr Pro
225                 230                 235                 240

Lys Glu Gln Ser Ile His Ser Arg Gly Thr His Ile Leu Thr Pro Glu
                245                 250                 255

Thr Glu Ala Ser Cys His Tyr Phe Phe Gly Ser Ser Arg Asn Phe Gly
            260                 265                 270
```

```
Ile Asp Asp Pro Glu Met Asp Gly Val Leu Arg Ser Trp Gln Ala Gln
        275                 280                 285

Ala Leu Val Lys Glu Asp Lys Val Val Glu Ala Ile Glu Arg Arg
    290                 295                 300

Arg Ala Tyr Val Glu Ala Asn Gly Ile Arg Pro Ala Met Leu Ser Cys
305                 310                 315                 320

Asp Glu Ala Ala Val Arg Val Ser Arg Glu Ile Glu Lys Leu Glu Gln
                325                 330                 335

Leu Glu Ala Ala
        340

<210> SEQ ID NO 37
<211> LENGTH: 1023
<212> TYPE: DNA
<213> ORGANISM: Artificial sequence
<220> FEATURE:
<223> OTHER INFORMATION: Synthetic DMO-Wmc(L) coding sequence

<400> SEQUENCE: 37
atgctcacct tcgttaggaa cgcctggtac gtcgccgctc tccctgagga gctgagcgag      60
aagcccttgg gtcgcaccat cctagacact ccgttagccc tttaccgcca gcctgacggc     120
gtagtggcgg ccctgcttga catctgcccg cataggttcg ctccgctcag cgacggcatc     180
ctcgtcaacg gcatcttca gtgcccgtac acgggctgg aatttgacgg cggtgggcag      240
tgtgtccaca cccgcacgg caacggcgca cggccagctt ccctcaacgt taggtcgttc      300
cctgttgtcg agcgcgacgc actgatctgg atctggcctg cgacccagc tctggccgat      360 ccaggagcca ttcccgactt cggttgccgc gtggacccag cctatcgac ggtcggcggt      420 tacgggcacg tcgattgtaa ctataagctc cttgtggaca accttatgga tttgggccac      480
gctcagtacg tgcaccgggc taacgctcag actgacgcct tgaccgtct cgaaagggag      540 gtcatcgtcg cgacggaga gattcaggcg ctgatgaaga tccctggagg cacgccctct      600
gtgctcatgg cgaagttct cagaggcgcg aacacgcccg tggacgcctg aacgacatc      660 cgctggaata aggtctccgc gatgctgaac ttcatcgccg ttgcgcccga ggcacaccc      720 aaagagcagt caatccacag cagagggacc catattctta caccggaaac cgaggctagt      780
tgccactact tcttcggctc gtcacggaat ttcgggatag cgatccgga gatggacggt      840 gttcttcgat cttggcaagc gcaagctctc gtcaaggaag ataaggtggt cgtggaggct      900
atcgagcgta ggcgcgccta cgttgaggcg aacggtatta ggcccgcgat gctgtcctgc      960
gacgaggccg cagttagagt gtcgcgcgag atagaaaagc tggagcagct agaggccgcc     1020
tga                                                                   1023

<210> SEQ ID NO 38
<211> LENGTH: 340
<212> TYPE: PRT
<213> ORGANISM: Artificial sequence
<220> FEATURE:
<223> OTHER INFORMATION: Modified dicamba monooxygenase sequence:
      DMO-Wmc(L)

<400

```
Ala Leu Tyr Arg Gln Pro Asp Gly Val Val Ala Ala Leu Leu Asp Ile
        35                  40                  45
Cys Pro His Arg Phe Ala Pro Leu Ser Asp Gly Ile Leu Val Asn Gly
    50                  55                  60
His Leu Gln Cys Pro Tyr His Gly Leu Glu Phe Asp Gly Gly Gly Gln
65                  70                  75                  80
Cys Val His Asn Pro His Gly Asn Gly Ala Arg Pro Ala Ser Leu Asn
                85                  90                  95
Val Arg Ser Phe Pro Val Val Glu Arg Asp Ala Leu Ile Trp Ile Trp
            100                 105                 110
Pro Gly Asp Pro Ala Leu Ala Asp Pro Gly Ala Ile Pro Asp Phe Gly
            115                 120                 125
Cys Arg Val Asp Pro Ala Tyr Arg Thr Val Gly Tyr Gly His Val
        130                 135                 140
Asp Cys Asn Tyr Lys Leu Leu Val Asp Asn Leu Met Asp Leu Gly His
145                 150                 155                 160
Ala Gln Tyr Val His Arg Ala Asn Ala Gln Thr Asp Ala Phe Asp Arg
                165                 170                 175
Leu Glu Arg Glu Val Ile Val Gly Asp Gly Glu Ile Gln Ala Leu Met
            180                 185                 190
Lys Ile Pro Gly Gly Thr Pro Ser Val Leu Met Ala Lys Phe Leu Arg
        195                 200                 205
Gly Ala Asn Thr Pro Val Asp Ala Trp Asn Asp Ile Arg Trp Asn Lys
    210                 215                 220
Val Ser Ala Met Leu Asn Phe Ile Ala Val Ala Pro Glu Gly Thr Pro
225                 230                 235                 240
Lys Glu Gln Ser Ile His Ser Arg Gly Thr His Ile Leu Thr Pro Glu
                245                 250                 255
Thr Glu Ala Ser Cys His Tyr Phe Phe Gly Ser Ser Arg Asn Phe Gly
            260                 265                 270
Ile Asp Asp Pro Glu Met Asp Gly Val Leu Arg Ser Trp Gln Ala Gln
        275                 280                 285
Ala Leu Val Lys Glu Asp Lys Val Val Val Glu Ala Ile Glu Arg Arg
    290                 295                 300
Arg Ala Tyr Val Glu Ala Asn Gly Ile Arg Pro Ala Met Leu Ser Cys
305                 310                 315                 320
Asp Glu Ala Ala Val Arg Val Ser Arg Glu Ile Glu Lys Leu Glu Gln
                325                 330                 335
Leu Glu Ala Ala
        340

<210> SEQ ID NO 39
<211> LENGTH: 1023
<212> TYPE: DNA
<213> ORGANISM: Artificial sequence
<220> FEATURE:
<223> OTHER INFORMATION: Synthetic DMO-Wmc(A) coding sequence

<400> SEQUENCE: 39
atggccacct tcgttaggaa cgcctggtac gtcgccgctc tccctgagga gctgagcgag      60
aagcccttgg tcgcaccat cctagacact ccgttagccc tttaccgcca gcctgacggc     120
gtagtggcgg ccctgcttga catctgcccg cataggttcg ctccgctcag cgacggcatc     180
ctcgtcaacg ggcatcttca gtgcccgtac cacgggctgg aatttgacgg cggtgggcag     240
tgtgtccaca acccgcacgg caacggcgca cggccagctt ccctcaacgt taggtcgttc     300
```

```
cctgttgtcg agcgcgacgc actgatctgg atctggcctg gcgacccagc tctggccgat    360
ccaggagcca ttcccgactt cggttgccgc gtggacccag cctatcggac ggtcggcggt    420
tacgggcacg tcgattgtaa ctataagctc cttgtggaca accttatgga tttgggccac    480
gctcagtacg tgcaccgggc taacgctcag actgacgcct tgaccgtctc gaaagggag     540
gtcatcgtcg cgacggaga gattcaggcg ctgatgaaga tccctggagg cacgccctct     600
gtgctcatgg cgaagtttct cagaggcgcg aacacgcccg tggacgcctg gaacgacatc    660
cgctggaata aggtctccgc gatgctgaac ttcatcgccg ttgcgcccga gggcacaccc    720
aaagagcagt caatccacag cagagggacc catattctta caccggaaac cgaggctagt    780
tgccactact tcttcggctc gtcacggaat ttcgggatag cgatccgga gatggacggt     840
gttcttcgat cttggcaagc gcaagctctc gtcaaggaag ataaggtggt cgtggaggct    900
atcgagcgta ggcgcgccta cgttgaggcg aacggtatta ggcccgcgat gctgtcctgc    960
gacgaggccg cagttagagt gtcgcgcgag atagaaaagc tggagcagct agaggccgcc   1020
tga                                                                 1023
```

<210> SEQ ID NO 40
<211> LENGTH: 340
<212> TYPE: PRT
<213> ORGANISM: Artificial sequence
<220> FEATURE:
<223> OTHER INFORMATION: Modified dicamba monooxygenase sequence:
      DMO-Wmc(A)

<400> SEQUENCE: 40

```
Met Ala Thr Phe Val Arg Asn Ala Trp Tyr Val Ala Ala Leu Pro Glu
1               5                   10                  15

Glu Leu Ser Glu Lys Pro Leu Gly Arg Thr Ile Leu Asp Thr Pro Leu
            20                  25                  30

Ala Leu Tyr Arg Gln Pro Asp Gly Val Val Ala Leu Leu Asp Ile
        35                  40                  45

Cys Pro His Arg Phe Ala Pro Leu Ser Asp Gly Ile Leu Val Asn Gly
    50                  55                  60

His Leu Gln Cys Pro Tyr His Gly Leu Glu Phe Asp Gly Gly Gly Gln
65                  70                  75                  80

Cys Val His Asn Pro His Gly Asn Gly Ala Arg Pro Ala Ser Leu Asn
                85                  90                  95

Val Arg Ser Phe Pro Val Val Glu Arg Asp Ala Leu Ile Trp Ile Trp
            100                 105                 110

Pro Gly Asp Pro Ala Leu Ala Asp Pro Gly Ala Ile Pro Asp Phe Gly
        115                 120                 125

Cys Arg Val Asp Pro Ala Tyr Arg Thr Val Gly Tyr Gly His Val
    130                 135                 140

Asp Cys Asn Tyr Lys Leu Leu Val Asp Asn Leu Met Asp Leu Gly His
145                 150                 155                 160

Ala Gln Tyr Val His Arg Ala Asn Ala Gln Thr Asp Ala Phe Asp Arg
                165                 170                 175

Leu Glu Arg Glu Val Ile Val Gly Asp Gly Glu Ile Gln Ala Leu Met
            180                 185                 190

Lys Ile Pro Gly Gly Thr Pro Ser Val Leu Met Ala Lys Phe Leu Arg
        195                 200                 205

Gly Ala Asn Thr Pro Val Asp Ala Trp Asn Asp Ile Arg Trp Asn Lys
    210                 215                 220
```

```
Val Ser Ala Met Leu Asn Phe Ile Ala Val Ala Pro Glu Gly Thr Pro
225                 230                 235                 240

Lys Glu Gln Ser Ile His Ser Arg Gly Thr His Ile Leu Thr Pro Glu
                245                 250                 255

Thr Glu Ala Ser Cys His Tyr Phe Phe Gly Ser Ser Arg Asn Phe Gly
            260                 265                 270

Ile Asp Asp Pro Glu Met Asp Gly Val Leu Arg Ser Trp Gln Ala Gln
        275                 280                 285

Ala Leu Val Lys Glu Asp Lys Val Val Glu Ala Ile Glu Arg Arg
    290                 295                 300

Arg Ala Tyr Val Glu Ala Asn Gly Ile Arg Pro Ala Met Leu Ser Cys
305                 310                 315                 320

Asp Glu Ala Ala Val Arg Val Ser Arg Glu Ile Glu Lys Leu Glu Gln
                325                 330                 335

Leu Glu Ala Ala
            340

<210> SEQ ID NO 41
<211> LENGTH: 433
<212> TYPE: DNA
<213> ORGANISM: Artificial Sequence
<220> FEATURE:
<223> OTHER INFORMATION: Modified Peanut Chlorotic Streak Virus (PClSV)
      promoter

<400> SEQUENCE: 41
agatcttgag ccaatcaaag aggagtgatg tagacctaaa gcaataatgg agccatgacg        60
taagggctta cgcccatacg aaataattaa aggctgatgt gacctgtcgg tctctcagaa       120
cctttacttt ttatgtttgg cgtgtatttt taaatttcca cggcaatgac gatgtgaccc       180
aacgagatct tgagccaatc aaagaggagt gatgtagacc taaagcaata atggagccat       240
gacgtaaggg cttacgccca tacgaaataa ttaaaggctg atgtgacctg tcggtctctc       300 agaacccttta cttttttatat ttggcgtgta tttttaaatt tccacggcaa tgacgatgtg    360
acctgtgcat ccgctttgcc tataaataag ttttagtttg tattgatcga cacggtcgag       420
aagacacggc cat                                                         433
```